(12) United States Patent
Schmidt et al.

(10) Patent No.: US 10,420,932 B2
(45) Date of Patent: Sep. 24, 2019

(54) LEADLESS CARDIAC PACEMAKER WITH RETRIEVAL FEATURES

(71) Applicant: CARDIAC PACEMAKERS, INC., St. Paul, MN (US)

(72) Inventors: Brian L. Schmidt, White Bear Lake, MN (US); Benjamin J. Haasl, Forest Lake, MN (US); John M. Edgell, Plymouth, MN (US); Dana Sachs, Pine City, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 74 days.

(21) Appl. No.: 15/705,766

(22) Filed: Sep. 15, 2017

(65) Prior Publication Data

US 2018/0001082 A1    Jan. 4, 2018

Related U.S. Application Data

(63) Continuation of application No. 14/698,490, filed on Apr. 28, 2015, now Pat. No. 9,795,781.

(60) Provisional application No. 61/985,788, filed on Apr. 29, 2014.

(51) Int. Cl.
*A61N 1/05* (2006.01)
*A61B 17/50* (2006.01)
*A61N 1/375* (2006.01)

(52) U.S. Cl.
CPC ............ *A61N 1/0587* (2013.01); *A61B 17/50* (2013.01); *A61N 1/3756* (2013.01)

(58) Field of Classification Search
CPC ..... A61B 17/50; A61N 1/0587; A61N 1/3756
See application file for complete search history.

(56) References Cited

U.S. PATENT DOCUMENTS

| | | |
|---|---|---|
| 721,869 A | 3/1903 | Dunning |
| 3,717,151 A | 2/1973 | Collett |
| 3,754,555 A | 8/1973 | Schmitt |
| 3,814,104 A | 6/1974 | Irnich et al. |
| 3,835,864 A | 9/1974 | Rasor et al. |
| 3,902,501 A | 9/1975 | Citron et al. |
| 3,943,936 A | 3/1976 | Rasor et al. |
| 3,971,364 A | 7/1976 | Fletcher et al. |
| 3,976,082 A | 8/1976 | Schmitt |
| 4,103,690 A | 8/1978 | Harris |

(Continued)

FOREIGN PATENT DOCUMENTS

| | | |
|---|---|---|
| CA | 1003904 A1 | 1/1977 |
| DE | 2053919 A1 | 5/1972 |

(Continued)

OTHER PUBLICATIONS

Spickler, et al. "Totally Self-Contained Interacardiac Pacemaker," J. Electrocardiology, vol. 3(3-4); 325-331, 1970.

*Primary Examiner* — Amanda K Hulbert
(74) *Attorney, Agent, or Firm* — Seager, Tufte & Wickhem LLP

(57) ABSTRACT

An implantable leadless cardiac pacing device and associated retrieval features. The implantable device includes a docking member extending from the proximal end of the housing of the implantable device including a covering surrounding at least a portion of the docking member configured to facilitate retrieval of the implantable leadless cardiac pacing device.

20 Claims, 16 Drawing Sheets

(56) References Cited

U.S. PATENT DOCUMENTS

| | | | |
|---|---|---|---|
| 4,112,952 | A | 9/1978 | Thomas et al. |
| 4,269,198 | A | 5/1981 | Stokes |
| 4,280,512 | A | 7/1981 | Karr et al. |
| 4,301,815 | A | 11/1981 | Doring |
| 4,402,328 | A | 9/1983 | Doring |
| 4,409,994 | A | 10/1983 | Doring |
| 4,502,492 | A | 3/1985 | Bomzin |
| 4,662,382 | A | 5/1987 | Sluetz et al. |
| 4,898,577 | A | 2/1990 | Badger et al. |
| 4,913,164 | A | 4/1990 | Greene et al. |
| 5,003,990 | A | 4/1991 | Osypka |
| 5,057,114 | A | 10/1991 | Wittich et al. |
| 5,129,749 | A | 7/1992 | Sato |
| 5,171,233 | A | 12/1992 | Amplatz et al. |
| 5,193,540 | A | 3/1993 | Schulman et al. |
| 5,257,634 | A | 11/1993 | Kroll |
| 5,282,845 | A | 2/1994 | Bush et al. |
| 5,300,107 | A | 4/1994 | Stokes et al. |
| 5,318,528 | A | 6/1994 | Heaven et al. |
| 5,336,253 | A | 8/1994 | Gordon et al. |
| 5,405,367 | A | 4/1995 | Schulman et al. |
| 5,405,374 | A | 4/1995 | Stein |
| 5,411,535 | A | 5/1995 | Fujii et al. |
| 5,425,756 | A | 6/1995 | Heil, Jr. et al. |
| 5,443,492 | A | 8/1995 | Stokes et al. |
| 5,492,119 | A | 2/1996 | Abrams |
| 5,522,875 | A | 6/1996 | Gates et al. |
| 5,522,876 | A | 6/1996 | Rusink |
| 5,545,201 | A | 8/1996 | Helland et al. |
| 5,545,206 | A | 8/1996 | Carson |
| 5,562,723 | A | 10/1996 | Rugland et al. |
| 5,575,814 | A | 11/1996 | Giele et al. |
| 5,578,068 | A | 11/1996 | Laske et al. |
| 5,697,936 | A | 12/1997 | Shipko et al. |
| 5,716,390 | A | 2/1998 | Li |
| 5,716,391 | A | 2/1998 | Grandjean |
| 5,755,764 | A | 5/1998 | Schroeppel |
| 5,776,178 | A | 7/1998 | Pohndorf et al. |
| 5,807,399 | A | 9/1998 | Laske et al. |
| 5,837,006 | A | 11/1998 | Ocel et al. |
| 5,837,007 | A | 11/1998 | Altman et al. |
| 5,851,226 | A | 12/1998 | Skubitz et al. |
| 5,871,531 | A | 2/1999 | Struble |
| 5,908,381 | A | 6/1999 | Aznoian et al. |
| 5,908,447 | A | 6/1999 | Schroeppel et al. |
| 6,041,258 | A | 3/2000 | Cigaina et al. |
| 6,055,457 | A | 4/2000 | Bonner |
| 6,074,401 | A | 6/2000 | Gardiner et al. |
| 6,078,840 | A | 6/2000 | Stokes |
| 6,093,177 | A | 7/2000 | Javier, Jr. et al. |
| 6,129,749 | A | 10/2000 | Bartig et al. |
| 6,132,456 | A | 10/2000 | Sommer et al. |
| 6,181,973 | B1 | 1/2001 | Ceron et al. |
| 6,188,932 | B1 | 2/2001 | Lindegren |
| 6,240,322 | B1 | 5/2001 | Peterfeso et al. |
| 6,251,104 | B1 | 6/2001 | Kesten et al. |
| 6,290,719 | B1 | 9/2001 | Garberoglio |
| 6,321,124 | B1 | 11/2001 | Cigaina |
| 6,322,548 | B1 | 11/2001 | Payne et al. |
| RE37,463 | E | 12/2001 | Altman |
| 6,358,256 | B1 | 3/2002 | Reinhardt |
| 6,363,938 | B2 | 4/2002 | Saadat et al. |
| 6,381,495 | B1 | 4/2002 | Jenkins |
| 6,381,500 | B1 | 4/2002 | Fischer, Sr. |
| 6,408,214 | B1 | 6/2002 | Williams et al. |
| 6,458,145 | B1 | 10/2002 | Ravenscroft et al. |
| 6,477,423 | B1 | 11/2002 | Jenkins |
| 6,500,182 | B2 | 12/2002 | Foster |
| 6,510,332 | B1 | 1/2003 | Greenstein |
| 6,510,345 | B1 | 1/2003 | Van Bentem |
| 6,522,915 | B1 | 2/2003 | Ceballos et al. |
| 6,572,587 | B2 | 6/2003 | Lerman et al. |
| 6,582,441 | B1 | 6/2003 | He et al. |
| 6,592,581 | B2 | 7/2003 | Bowe |
| 6,623,518 | B2 | 9/2003 | Thompson et al. |
| 6,626,915 | B2 | 9/2003 | Leveillee |
| 6,638,268 | B2 | 10/2003 | Niazi |
| 6,684,109 | B1 | 1/2004 | Osypka |
| 6,711,443 | B2 | 3/2004 | Osypka |
| 6,743,240 | B2 | 6/2004 | Smith et al. |
| 6,755,812 | B2 | 6/2004 | Peterson et al. |
| 6,909,920 | B2 | 6/2005 | Lokhoff et al. |
| 6,944,507 | B2 | 9/2005 | Fröberg et al. |
| 6,953,454 | B2 | 10/2005 | Peterson et al. |
| 7,027,876 | B2 | 4/2006 | Casavant et al. |
| 7,082,335 | B2 | 7/2006 | Klein et al. |
| 7,085,606 | B2 | 8/2006 | Flach et al. |
| 7,092,765 | B2 | 8/2006 | Geske et al. |
| 7,092,766 | B1 | 8/2006 | Salys et al. |
| 7,120,504 | B2 | 10/2006 | Osypka |
| 7,149,587 | B2 | 12/2006 | Wardle et al. |
| 7,158,838 | B2 | 1/2007 | Seifert et al. |
| 7,162,310 | B2 | 1/2007 | Doan |
| 7,181,288 | B1 | 2/2007 | Rezai et al. |
| 7,187,982 | B2 | 3/2007 | Seifert et al. |
| 7,200,437 | B2 | 4/2007 | Nabutovsky et al. |
| 7,212,869 | B2 | 5/2007 | Wahlstrom et al. |
| 7,229,415 | B2 | 6/2007 | Schwartz |
| 7,251,532 | B2 | 7/2007 | Hess et al. |
| 7,289,853 | B1 | 10/2007 | Campbell et al. |
| 7,313,445 | B2 | 12/2007 | McVenes et al. |
| 7,326,231 | B2 | 2/2008 | Phillips et al. |
| 7,328,071 | B1 | 2/2008 | Stehr et al. |
| 7,383,091 | B1 | 6/2008 | Chitre et al. |
| 7,450,999 | B1 | 11/2008 | Karicherla et al. |
| 7,462,184 | B2 | 12/2008 | Worley et al. |
| 7,463,933 | B2 | 12/2008 | Wahlstrom et al. |
| 7,499,758 | B2 | 3/2009 | Cates et al. |
| 7,509,169 | B2 | 3/2009 | Eigler et al. |
| 7,515,971 | B1 | 4/2009 | Doan |
| 7,532,939 | B2 | 5/2009 | Sommer et al. |
| 7,558,631 | B2 | 7/2009 | Cowan et al. |
| 7,634,319 | B2 | 12/2009 | Schneider et al. |
| 7,647,109 | B2 | 1/2010 | Hastings et al. |
| 7,657,325 | B2 | 2/2010 | Williams |
| 7,678,128 | B2 | 3/2010 | Boyle et al. |
| 7,717,899 | B2 | 5/2010 | Bowe et al. |
| 7,731,655 | B2 | 6/2010 | Smith et al. |
| 7,734,343 | B2 | 6/2010 | Ransbury et al. |
| 7,740,640 | B2 | 6/2010 | Ginn |
| 7,785,264 | B2 | 8/2010 | Hettrick et al. |
| 7,799,037 | B1 | 9/2010 | He et al. |
| 7,801,624 | B1 | 9/2010 | Flannery et al. |
| 7,835,801 | B1 | 11/2010 | Sundararajan et al. |
| 7,840,281 | B2 | 11/2010 | Kveen et al. |
| 7,840,283 | B1 | 11/2010 | Bush et al. |
| 7,860,580 | B2 | 12/2010 | Falk et al. |
| 7,875,049 | B2 | 1/2011 | Eversull et al. |
| 7,890,186 | B2 | 2/2011 | Wardle et al. |
| 7,904,179 | B2 | 3/2011 | Rutten et al. |
| 7,920,928 | B1 | 4/2011 | Yang et al. |
| 7,993,351 | B2 | 8/2011 | Worley et al. |
| 8,010,209 | B2 | 8/2011 | Jacobson |
| 8,036,757 | B2 | 10/2011 | Worley |
| 8,057,486 | B2 | 11/2011 | Hansen |
| 8,082,035 | B2 | 12/2011 | Glukhovsky |
| 8,103,361 | B2 | 1/2012 | Moser |
| 8,108,054 | B2 | 1/2012 | Helland |
| 8,142,347 | B2 | 3/2012 | Griego et al. |
| 8,160,722 | B2 | 4/2012 | Rutten et al. |
| 8,185,213 | B2 | 5/2012 | Kveen et al. |
| 8,219,213 | B2 | 7/2012 | Sommer et al. |
| 8,233,994 | B2 | 7/2012 | Sommer et al. |
| 8,252,019 | B2 | 8/2012 | Flemming, III |
| 8,295,939 | B2 | 10/2012 | Jacobson |
| 8,313,445 | B2 | 11/2012 | Mishima et al. |
| 8,352,025 | B2 | 1/2013 | Jacobson |
| 8,352,028 | B2 | 1/2013 | Wenger |
| 8,364,277 | B2 | 1/2013 | Glukhovsky |
| 8,364,280 | B2 | 1/2013 | Marnfeldt et al. |
| 8,406,900 | B2 | 3/2013 | Barlov et al. |
| 8,406,901 | B2 | 3/2013 | Starkebaum et al. |
| 8,428,750 | B2 | 4/2013 | Kolberg |
| 8,452,420 | B2 | 5/2013 | Flach et al. |

(56) References Cited

U.S. PATENT DOCUMENTS

| | | |
|---|---|---|
| 8,478,431 B2 | 7/2013 | Griswold et al. |
| 8,489,189 B2 | 7/2013 | Tronnes |
| 8,494,650 B2 | 7/2013 | Glukhovsky et al. |
| 8,504,156 B2 | 8/2013 | Bonner et al. |
| 8,518,060 B2 | 8/2013 | Jelich et al. |
| 8,527,068 B2 | 9/2013 | Ostroff |
| 8,532,790 B2 | 9/2013 | Griswold |
| 8,548,605 B2 | 10/2013 | Ollivier |
| 8,565,897 B2 | 10/2013 | Regnier et al. |
| 8,615,310 B2 | 12/2013 | Khairkhahan et al. |
| 8,634,912 B2 | 1/2014 | Bornzin et al. |
| 8,670,842 B1 | 3/2014 | Bornzin et al. |
| 8,721,587 B2 | 5/2014 | Berthiaume et al. |
| 8,758,365 B2 | 6/2014 | Bonner et al. |
| 9,727,996 B2 | 8/2017 | Pandey et al. |
| 9,795,781 B2 | 10/2017 | Schmidt et al. |
| 2002/0077556 A1 | 6/2002 | Schwartz |
| 2003/0004537 A1 | 1/2003 | Boyle et al. |
| 2004/0176797 A1 | 9/2004 | Opolski |
| 2005/0090890 A1 | 4/2005 | Wu et al. |
| 2005/0267555 A1 | 12/2005 | Marnfeldt et al. |
| 2006/0247753 A1 | 11/2006 | Wenger et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0233218 A1 | 10/2007 | Kolberg |
| 2007/0239248 A1 | 10/2007 | Hastings et al. |
| 2007/0255376 A1 | 11/2007 | Michels et al. |
| 2007/0276444 A1 | 11/2007 | Gelbart et al. |
| 2007/0293904 A1 | 12/2007 | Gelbart et al. |
| 2008/0021532 A1 | 1/2008 | Kveen et al. |
| 2009/0082828 A1 | 3/2009 | Ostroff |
| 2009/0281605 A1 | 11/2009 | Marnfeldt et al. |
| 2010/0198288 A1 | 8/2010 | Ostroff |
| 2011/0034939 A1 | 2/2011 | Kveen et al. |
| 2011/0112548 A1 | 5/2011 | Fifer et al. |
| 2011/0125163 A1 | 5/2011 | Ruffen et al. |
| 2011/0190785 A1 | 8/2011 | Gerber et al. |
| 2011/0190786 A1 | 8/2011 | Gerber et al. |
| 2011/0208260 A1 | 8/2011 | Jacobson |
| 2011/0237967 A1 | 9/2011 | Moore et al. |
| 2011/0270339 A1 | 11/2011 | Murray, III et al. |
| 2011/0270340 A1 | 11/2011 | Pellegrini et al. |
| 2011/0282423 A1 | 11/2011 | Jacobson |
| 2011/0307043 A1 | 12/2011 | Ollivier |
| 2012/0078322 A1 | 3/2012 | Dal Molin et al. |
| 2012/0078336 A1 | 3/2012 | Helland |
| 2012/0095539 A1 | 4/2012 | Khairkhahan et al. |
| 2012/0109002 A1 | 5/2012 | Mothilal et al. |
| 2012/0109079 A1 | 5/2012 | Asleson et al. |
| 2012/0109148 A1 | 5/2012 | Bonner et al. |
| 2012/0109149 A1 | 5/2012 | Bonner et al. |
| 2012/0116489 A1 | 5/2012 | Khairkhahan et al. |
| 2012/0158111 A1 | 6/2012 | Khairkhahan et al. |
| 2012/0165827 A1* | 6/2012 | Khairkhahan ......... A61N 1/362 606/129 |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0197373 A1 | 8/2012 | Khairkhahan et al. |
| 2012/0232565 A1 | 9/2012 | Kveen et al. |
| 2012/0271134 A1 | 10/2012 | Allan et al. |
| 2012/0330392 A1 | 12/2012 | Regnier et al. |
| 2013/0006261 A1 | 1/2013 | Lampropoulos et al. |
| 2013/0006262 A1 | 1/2013 | Lampropoulos et al. |
| 2013/0012925 A1 | 1/2013 | Berthiaume et al. |
| 2013/0035636 A1 | 2/2013 | Beasley et al. |
| 2013/0035748 A1 | 2/2013 | Bonner et al. |
| 2013/0053921 A1 | 2/2013 | Bonner et al. |
| 2013/0079798 A1 | 3/2013 | Tran et al. |
| 2013/0079861 A1 | 3/2013 | Reinert et al. |
| 2013/0103047 A1 | 4/2013 | Steingisser et al. |
| 2013/0103049 A1 | 4/2013 | Bonde |
| 2013/0116741 A1 | 5/2013 | Bomzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0296957 A1 | 11/2013 | Tronnes |
| 2014/0058494 A1 | 2/2014 | Ostroff et al. |
| 2014/0074114 A1 | 3/2014 | Khairkhahan et al. |
| 2014/0148815 A1 | 5/2014 | Wenzel et al. |
| 2014/0180306 A1 | 6/2014 | Grubac et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0306381 A1 | 10/2015 | Schmidt et al. |

FOREIGN PATENT DOCUMENTS

| | | |
|---|---|---|
| EP | 0779080 B1 | 5/2003 |
| JP | 05245215 A | 9/1993 |
| WO | 03032807 A2 | 4/2003 |
| WO | 2009039400 A1 | 3/2009 |
| WO | 2012092067 A1 | 7/2012 |
| WO | 2012092074 A1 | 7/2012 |
| WO | 2015023473 A1 | 2/2015 |

* cited by examiner

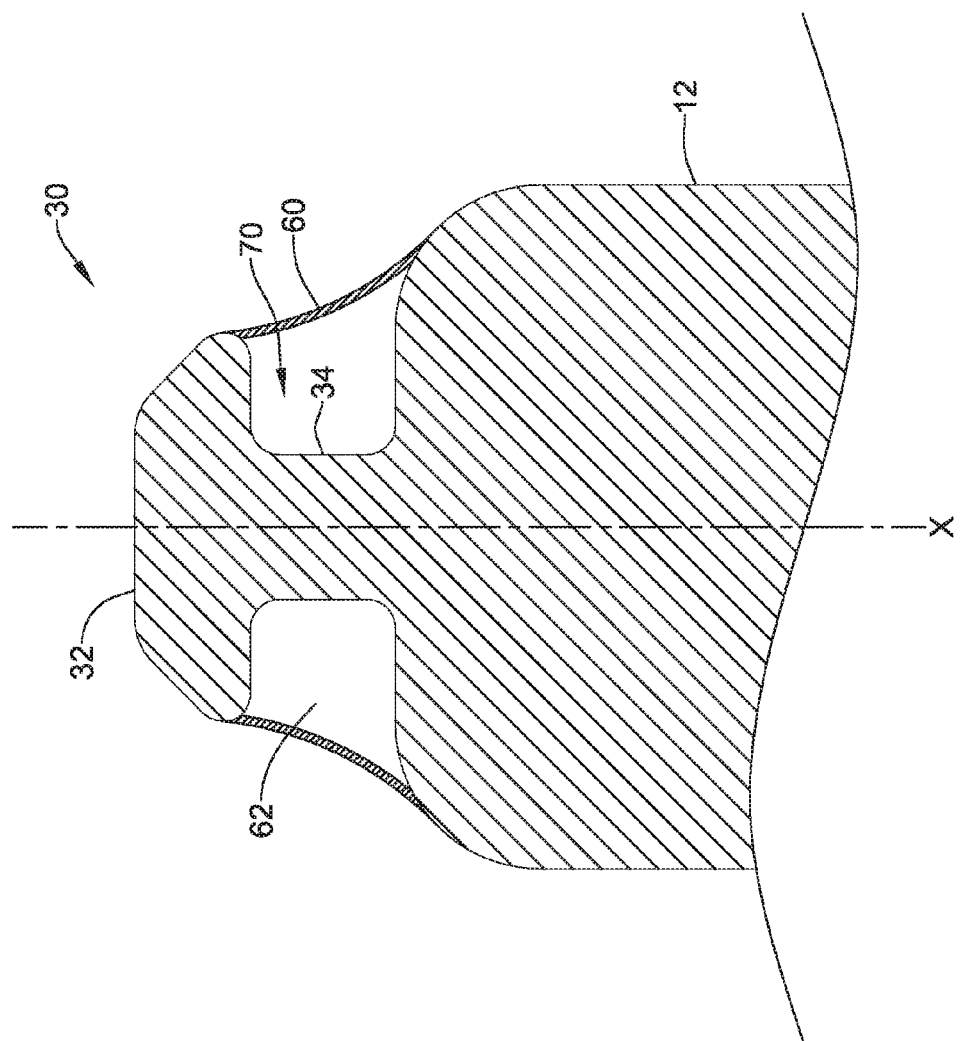

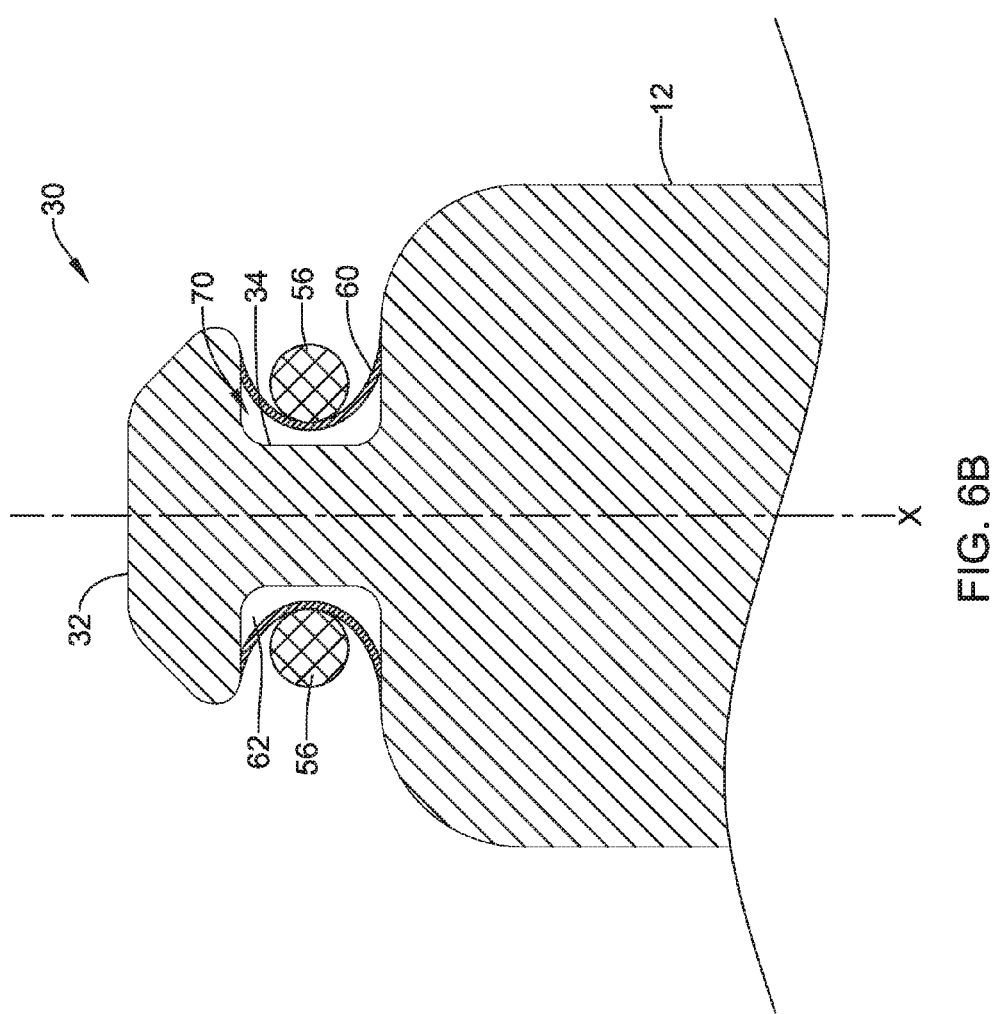

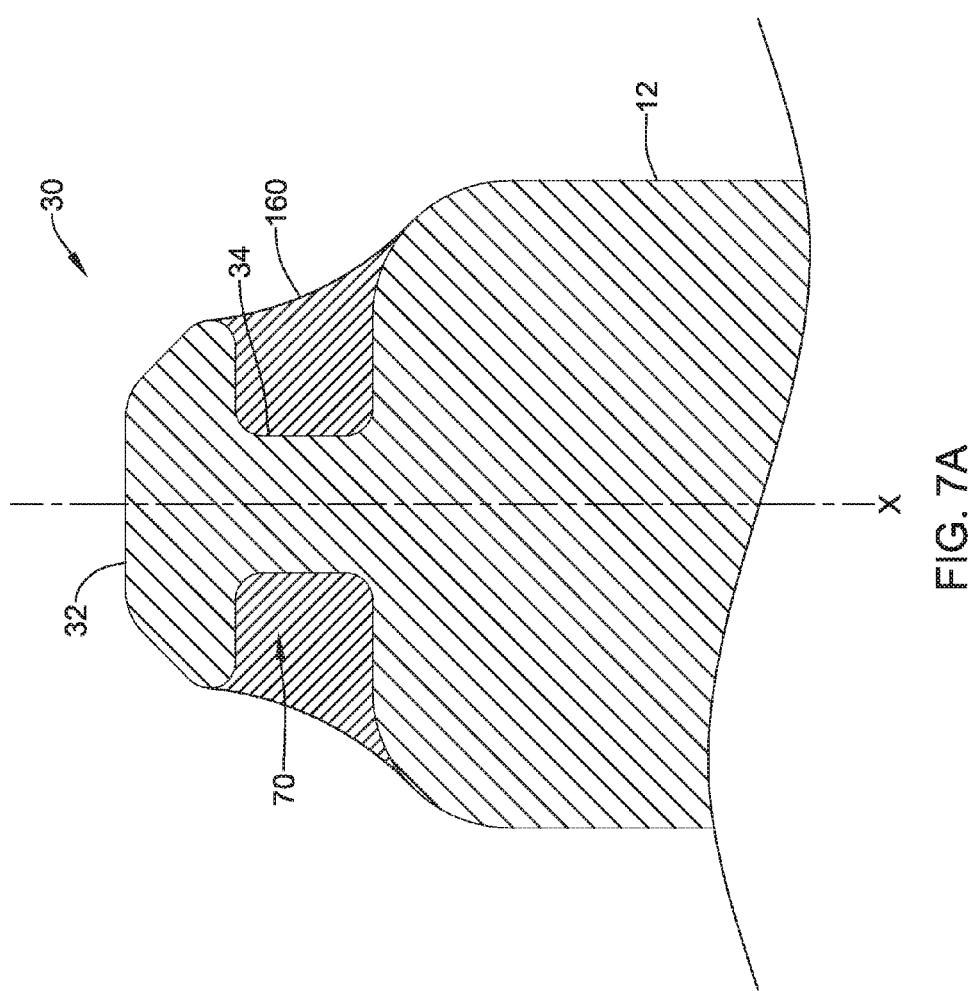

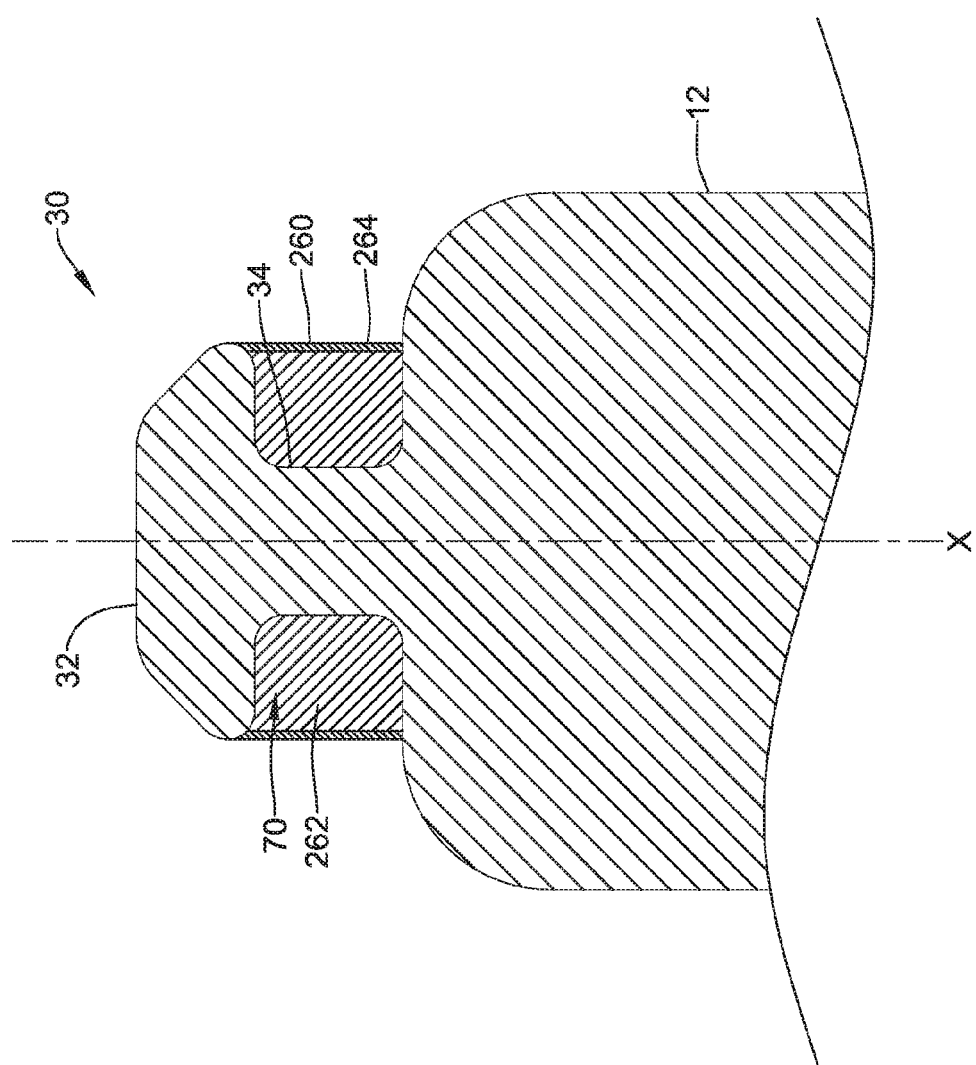

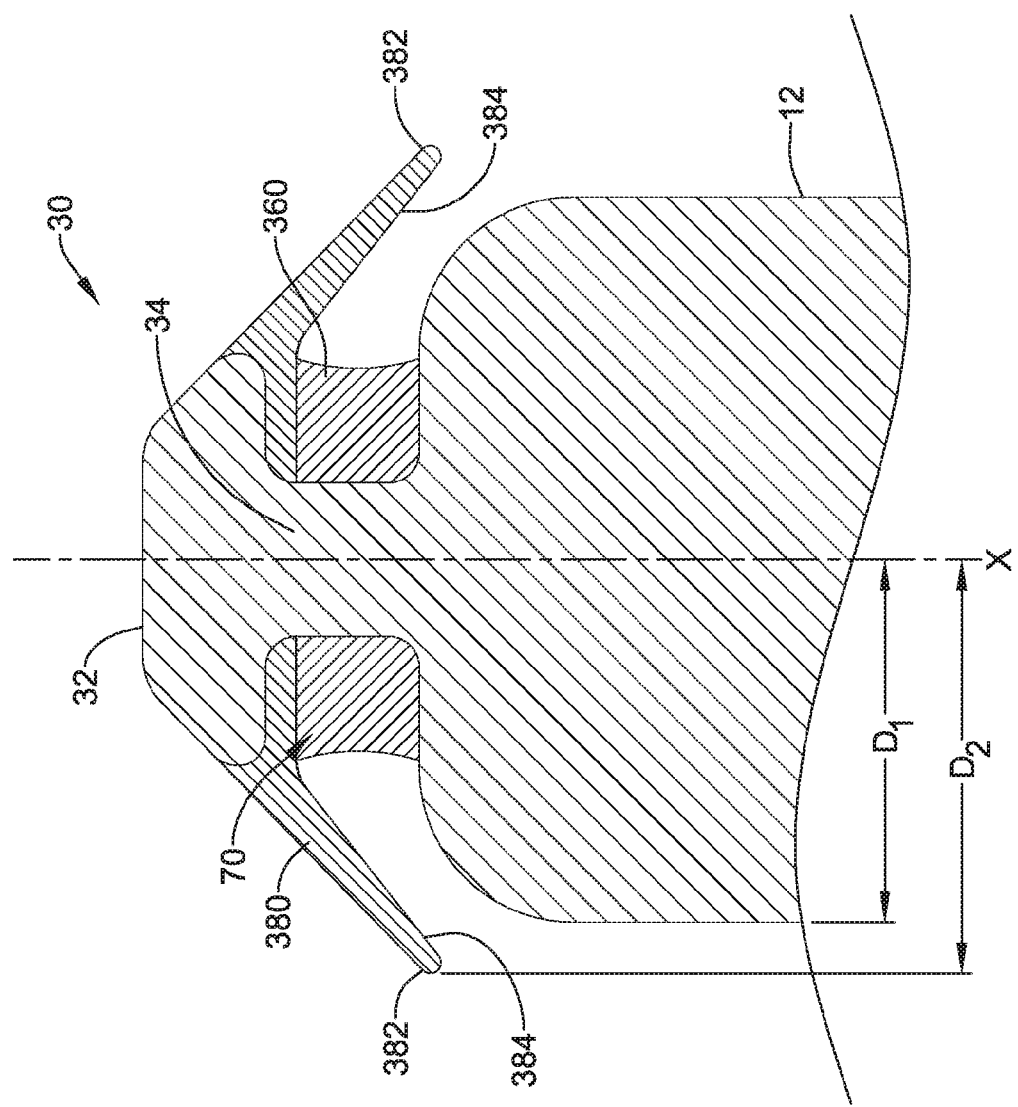

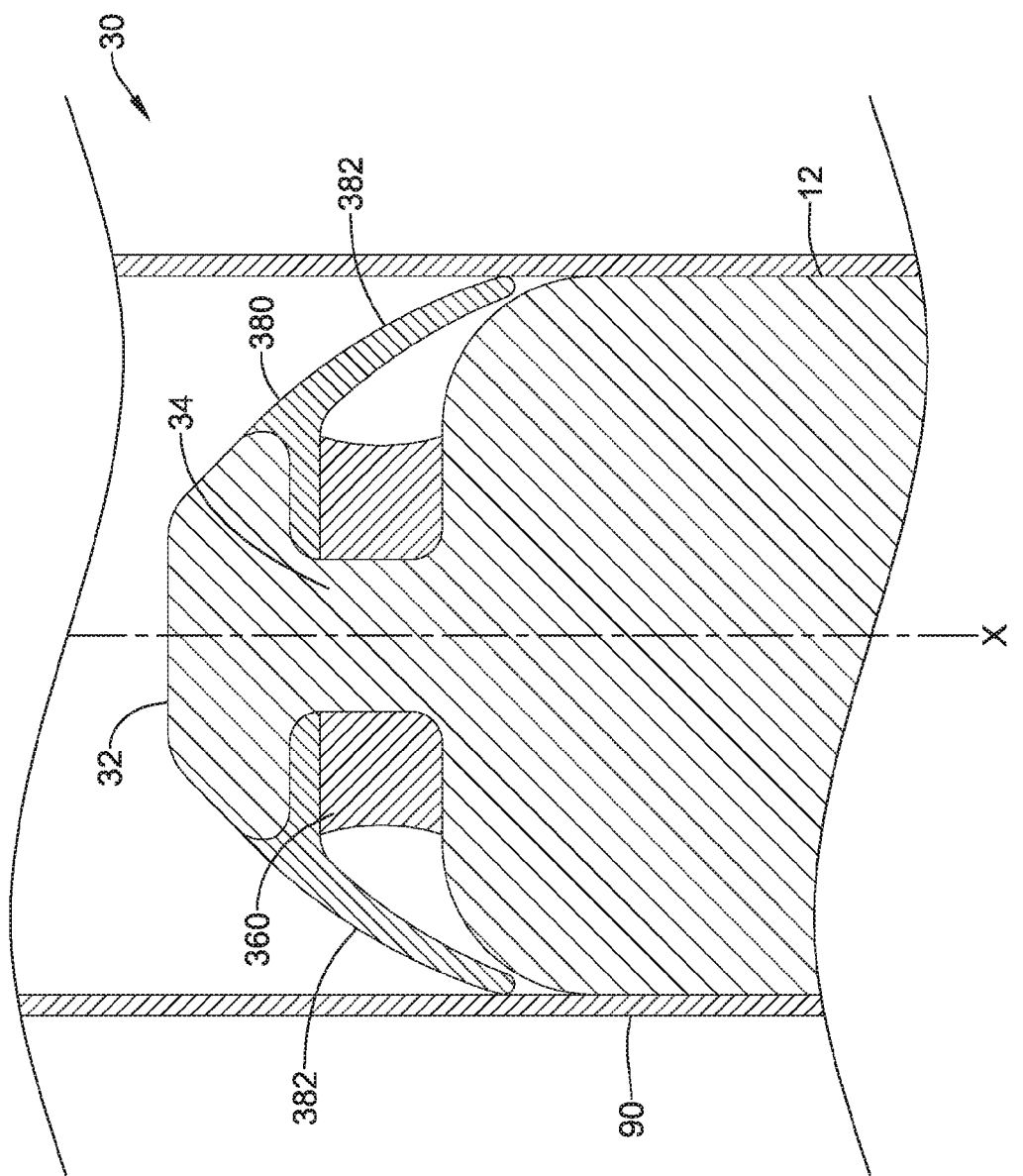

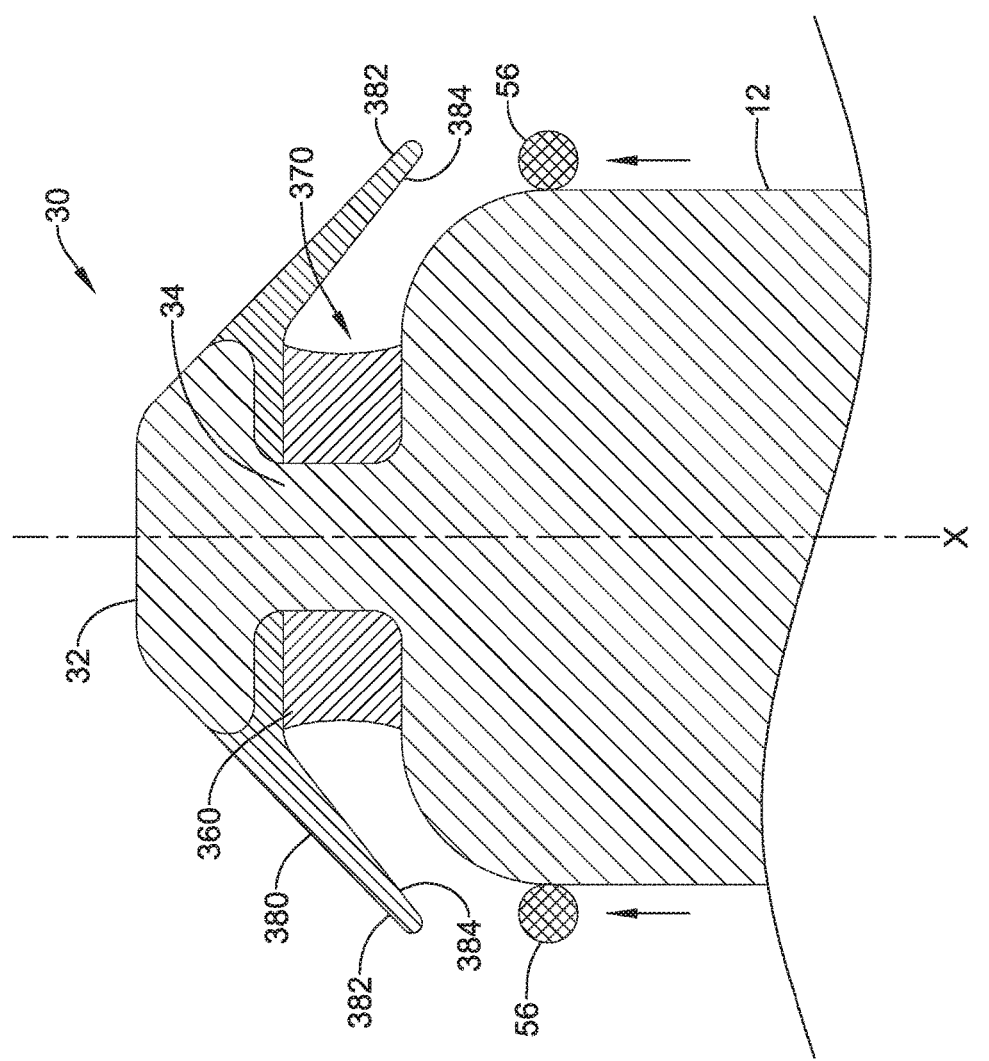

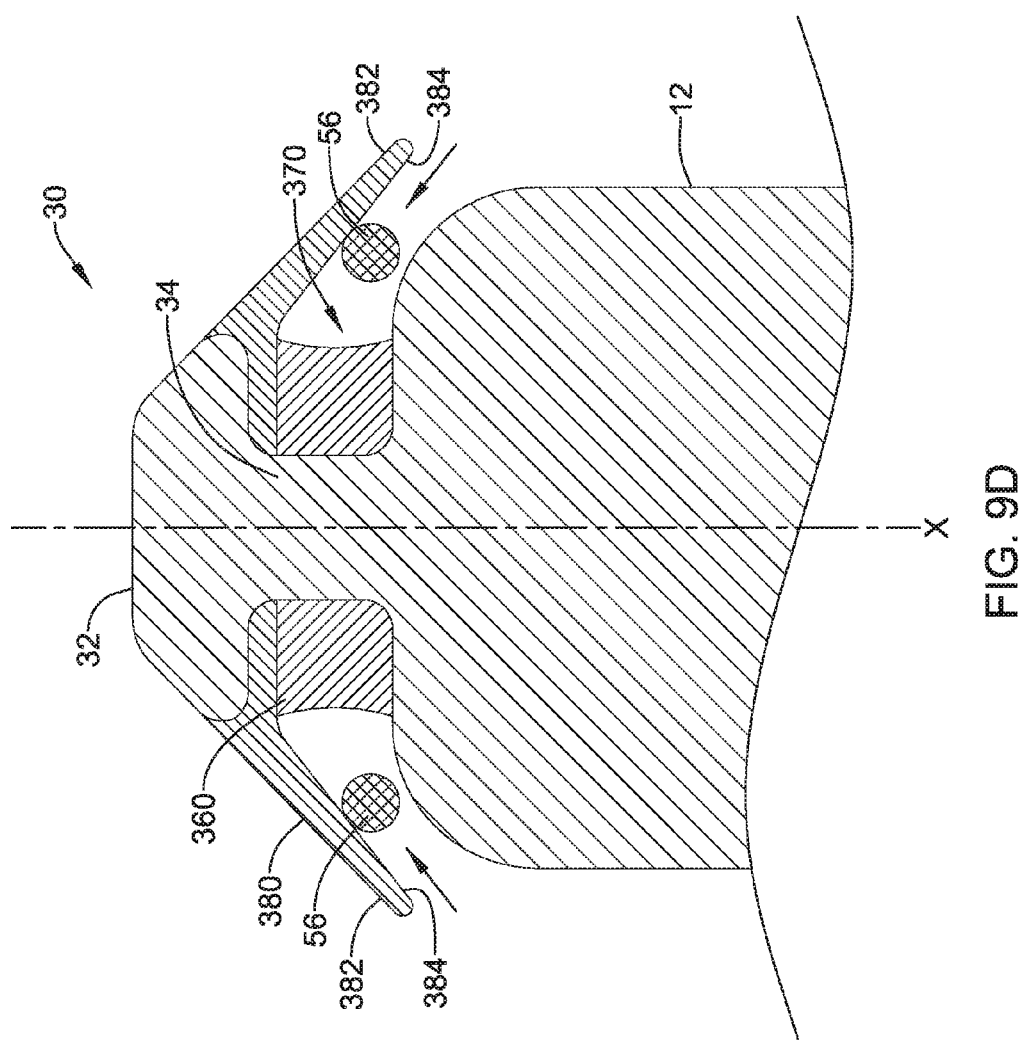

LEADLESS CARDIAC PACEMAKER WITH RETRIEVAL FEATURES

CROSS REFERENCE TO RELATED APPLICATIONS

The present application is a continuation application of U.S. patent application Ser. No. 14/698,490, filed Apr. 28, 2015, which claims the benefit of U.S. Provisional Application Ser. No. 61/985,788, filed Apr. 29, 2014, the complete disclosures of which are herein incorporated by reference.

TECHNICAL FIELD

The disclosure is directed to implantable cardiac devices. More particularly, the disclosure is directed to leadless cardiac stimulators or pacemakers including retrieval features, such as a collar or covering associated with a proximal docking member.

BACKGROUND

Cardiac pacemakers provide electrical stimulation to heart tissue to cause the heart to contract and thus pump blood through the vascular system. Conventional pacemakers typically include an electrical lead that extends from a pulse generator implanted subcutaneously or sub-muscularly to an electrode positioned adjacent the inside or outside wall of the cardiac chamber. As an alternative to conventional pacemakers, self-contained or leadless cardiac pacemakers have been proposed. Leadless cardiac pacemakers are small capsules typically fixed to an intracardiac implant site in a cardiac chamber with a fixation mechanism engaging the intracardiac tissue. The small capsule typically includes bipolar pacing/sensing electrodes, a power source (e.g. a battery), and associated electrical circuitry for controlling the pacing/sensing electrodes, and thus provide electrical stimulation to heart tissue and/or sense a physiological condition.

Accordingly, it is desirable to provide alternative structures to facilitate retrieving leadless cardiac pacemakers from an implantation site in a heart chamber.

SUMMARY

The disclosure is directed to several alternative designs, materials and methods of manufacturing medical device structures and assemblies, and uses thereof.

Accordingly one illustrative embodiment includes an implantable leadless cardiac pacing device including a housing having a proximal end and a distal end, an electrode positioned proximate the distal end of the housing configured to be positioned adjacent cardiac tissue, and a docking member extending from the proximal end of the housing along a longitudinal axis of the housing. The docking member is configured to facilitate retrieval of the implantable leadless cardiac pacing device. The docking member includes a head portion and a neck portion extending between the housing and the head portion. The head portion has a radial dimension from the longitudinal axis and the neck portion has a radial dimension from the longitudinal axis less than the radial dimension of the head portion. A covering surrounds at least a portion of the neck portion of the docking member.

Another illustrative embodiment includes an implantable leadless cardiac pacing device including a housing having a proximal end and a distal end, an electrode positioned proximate the distal end of the housing configured to be positioned adjacent cardiac tissue, and a docking member extending from the proximal end of the housing along a longitudinal axis of the housing. The docking member is configured to facilitate retrieval of the implantable leadless cardiac pacing device. The docking member includes a head portion and a neck portion extending between the housing and the head portion. The head portion has a radial dimension from the longitudinal axis and the neck portion has a radial dimension from the longitudinal axis less than the radial dimension of the head portion. A collapsible covering is located between the head portion of the docking member and the proximal end of the housing. The collapsible covering has a peripheral surface collapsible toward the neck portion when engaged with a retrieval device.

Yet another illustrative embodiment includes a method of retrieving an implantable cardiac pacing device. The implantable cardiac pacing device has a housing having a longitudinal axis, an electrode positioned proximate a distal end of the housing, and a docking member extending from a proximal end of the housing opposite the distal end. The docking member includes a head portion, a neck portion extending between the housing and the head portion, and a covering surrounding at least a portion of the neck portion. The method includes advancing a snare toward the docking member and encircling the docking member with a loop of the snare. The loop is then cinched around the neck portion of the docking member such that the covering collapses toward the longitudinal axis as the loop presses against the covering. In some instances, the covering collapses to a radial extent from the longitudinal axis less than an outermost radial extent of the head portion of the docking member from the longitudinal axis.

The above summary of some example embodiments is not intended to describe each disclosed embodiment or every implementation of the aspects of the disclosure.

BRIEF DESCRIPTION OF THE DRAWINGS

The aspects of the disclosure may be more completely understood in consideration of the following detailed description of various embodiments in connection with the accompanying drawings, in which:

FIGS. 6A-6B illustrate an exemplary covering for a docking member of an implantable device;

FIGS. 7A-7B illustrate another exemplary covering for a docking member of an implantable device;

FIGS. 8A-8B illustrate another exemplary covering for a docking member of an implantable device; and FIGS. 9A-9E illustrate another exemplary covering for a docking member of an implantable device.

Figure 1:
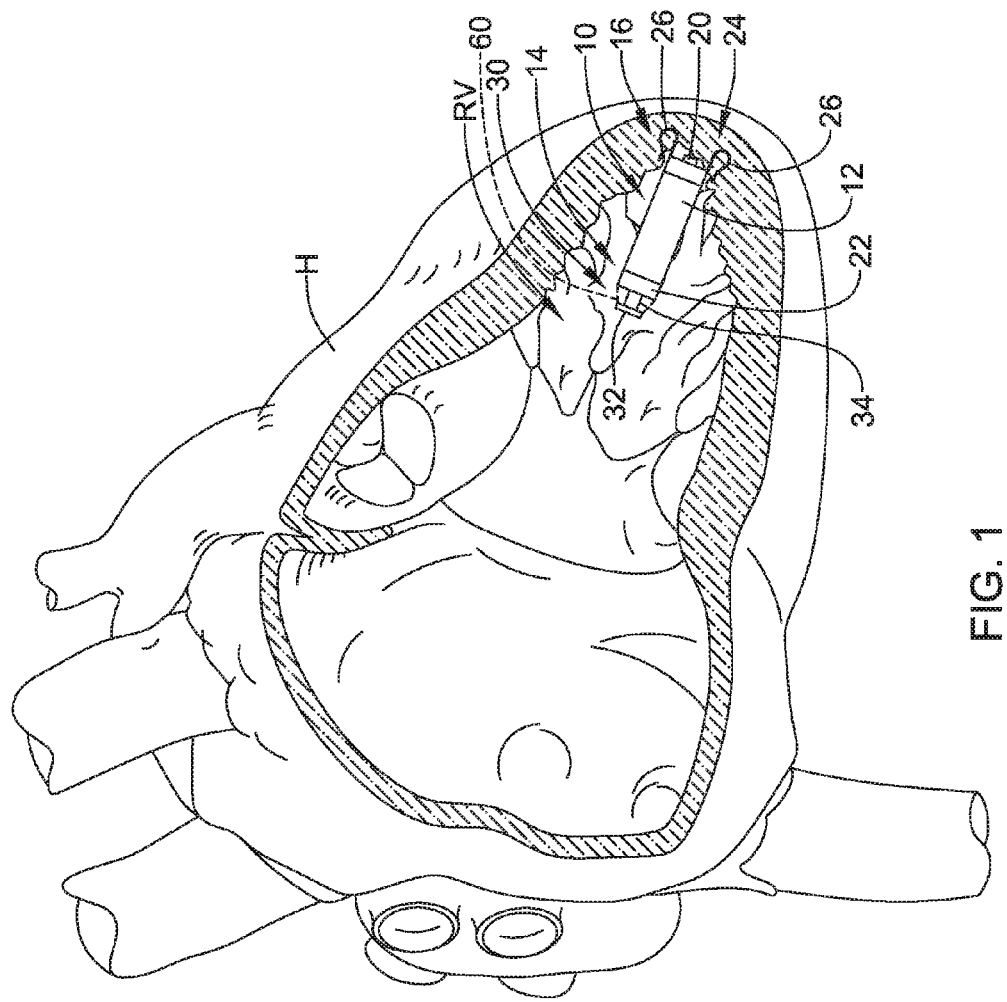
FIG. 1 illustrates an exemplary implantable device implanted in a chamber of a heart.

While the aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

Referring to FIG. 1, an exemplary implantable leadless cardiac pacing device 10 (e.g., a leadless pacemaker) is illustrated implanted in a chamber of a heart H, such as the apex of the right ventricle RV. The implantable device 10 may include a shell or housing 12 having a proximal end 14 and a distal end 16. The implantable device 10 may include a first electrode 20 positioned proximate the distal end 16 of the housing 12 and a second electrode 22 positioned proximate the proximal end 14 of the housing 12. The electrodes 20, 22 may be sensing and/or pacing electrodes to provide electro-therapy and/or sensing capabilities. The first electrode 20 may be configured to be positioned against or otherwise contact the cardiac tissue of the heart H while the second electrode 22 may be spaced away from the first electrode 20, and thus spaced away from the cardiac tissue.

The implantable device 10 may include a pulse generator (e.g., electrical circuitry) and a power source (e.g., a battery) within the housing 12 to provide electrical signals to the electrodes 20, 22 and thus control the pacing/sensing electrodes 20, 22. Electrical communication between pulse generator and the electrodes 20, 22 may provide electrical stimulation to heart tissue and/or sense a physiological condition.

The implantable device 10 may include a fixation mechanism 24 proximate the distal end 16 of the housing 12 configured to attach the implantable device 10 to a tissue wall of the heart H, or otherwise anchor the implantable device 10 to the anatomy of the patient. As shown in FIG. 1, in some instances, the fixation mechanism 24 may include one or more, or a plurality of hooks 26 anchored into the cardiac tissue of the heart H to attach the implantable device 10 to a tissue wall. In other instances, the fixation mechanism 24 may include one or more, or a plurality of passive tines, configured to entangle with trabeculae within the chamber of the heart H and/or a helical fixation anchor configured to be screwed into a tissue wall to anchor the implantable device 10 to the heart H.

The implantable device 10 may include a docking member 30 proximate the proximal end 14 of the housing 12 configured to facilitate delivery and/or retrieval of the implantable device 10. For example, the docking member 30 may extend from the proximal end 14 of the housing 12 along a longitudinal axis of the housing 12. The docking member 30 may include a head portion 32 and a neck portion 34 extending between the housing 12 and the head portion 32. The head portion 32 may be an enlarged portion relative to the neck portion 34. For example, the head portion 32 may have a radial dimension from the longitudinal axis of the implantable device 10 which is greater than a radial dimension of the neck portion from the longitudinal axis of the implantable device 10. The docking member 30 may be configured to facilitate delivery of the implantable device 10 to the intracardiac site and/or retrieval of the implantable device 10 from the intracardiac site. Some exemplary embodiments of the docking member 30 are described in further detail herein.

The implantable device 10 may also include a covering 60 surrounding at least a portion of the neck portion 34 of the docking member 30. For example, the covering 60 may extend from the head portion 34 of the docking member 30 to the proximal end of the housing 12, in some instances. The covering 60 may be collapsible radially inward toward the longitudinal axis, and thus toward the neck portion 34. In some instances, the covering 60 may be provided to preclude blood coagulation or embolization around the neck portion 34 while implanted in a patient, yet resilient to permit a snare or other retrieval device to cinch around the neck portion 34 during a retrieval procedure.

Figure 2:
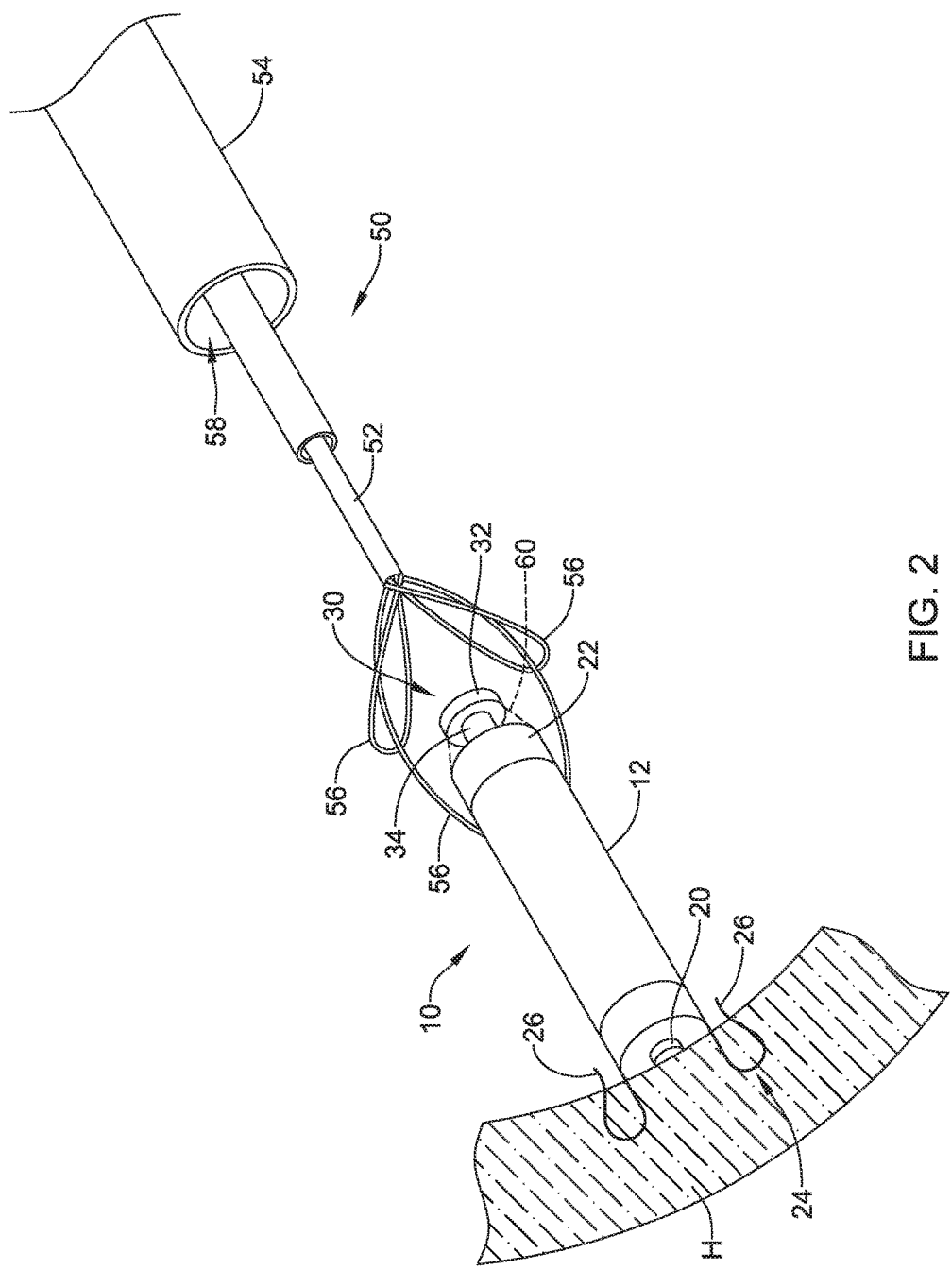
FIG. 2 illustrates an exemplary retrieval device capturing an implantable device during a retrieval procedure.

If it is desired to retrieve the implantable device 10 from the heart H, a retrieval device 50 may be advanced into the chamber of the heart H to capture the implantable device 10 and remove the implantable device 10 from the heart H. One exemplary retrieval device 50 is illustrated in FIG. 2. The retrieval device 50 may include a snare 52 advanceable from a lumen 58 of a retrieval catheter 54. The snare 52 may include one or more, or a plurality of loops 56 extending from a distal end of the snare 52 configured to engage the docking member 30 of the implantable device 10. The snare 52 shown in FIG. 2 includes three loops 56 formed by elongate filaments extending from the shaft of the snare 52. Once the loop(s) 56 of the snare 52 has captured the docking member 30, the snare 52 may be actuated proximally relative to the retrieval catheter 54 to pull the implantable device 10 into the lumen 58 of the retrieval catheter 54. The enlarged size of the head portion 32 relative to the neck portion 34 may permit the loop 56 of the snare 52 to encircle the neck portion 34 below (i.e., distal of) the head portion 32 and retain the loop 56 around the docking member 30 as the snare 52 is pulled proximally.

The loop of the snare 56 may collapse the covering 60 radially inward toward the neck portion 34 as the loop of the snare is cinched around the neck portion 34. The resiliency of the covering 60 may permit the loop of the snare 56 or other retrieval device to cinch around the neck portion 34 distal of the head portion 32 to secure the snare 56 with the docking member 30 to apply a retrieval force to pull the implantable device 10 into the retrieval catheter 54.

As the implantable device 10 is pulled into the retrieval catheter 54, the fixation mechanism 24 may disengage from the heart tissue to detach the implantable device 10 from the heart wall. For example, the hooks 26 may elongate as the implantable device 10 is drawn proximally into the lumen 58 of the retrieval catheter 54. Thereafter, the retrieval device 50, with the implantable device 10 captured in the lumen of the retrieval catheter 54 with the snare 52, may be withdrawn from the heart H.

Figure 3:
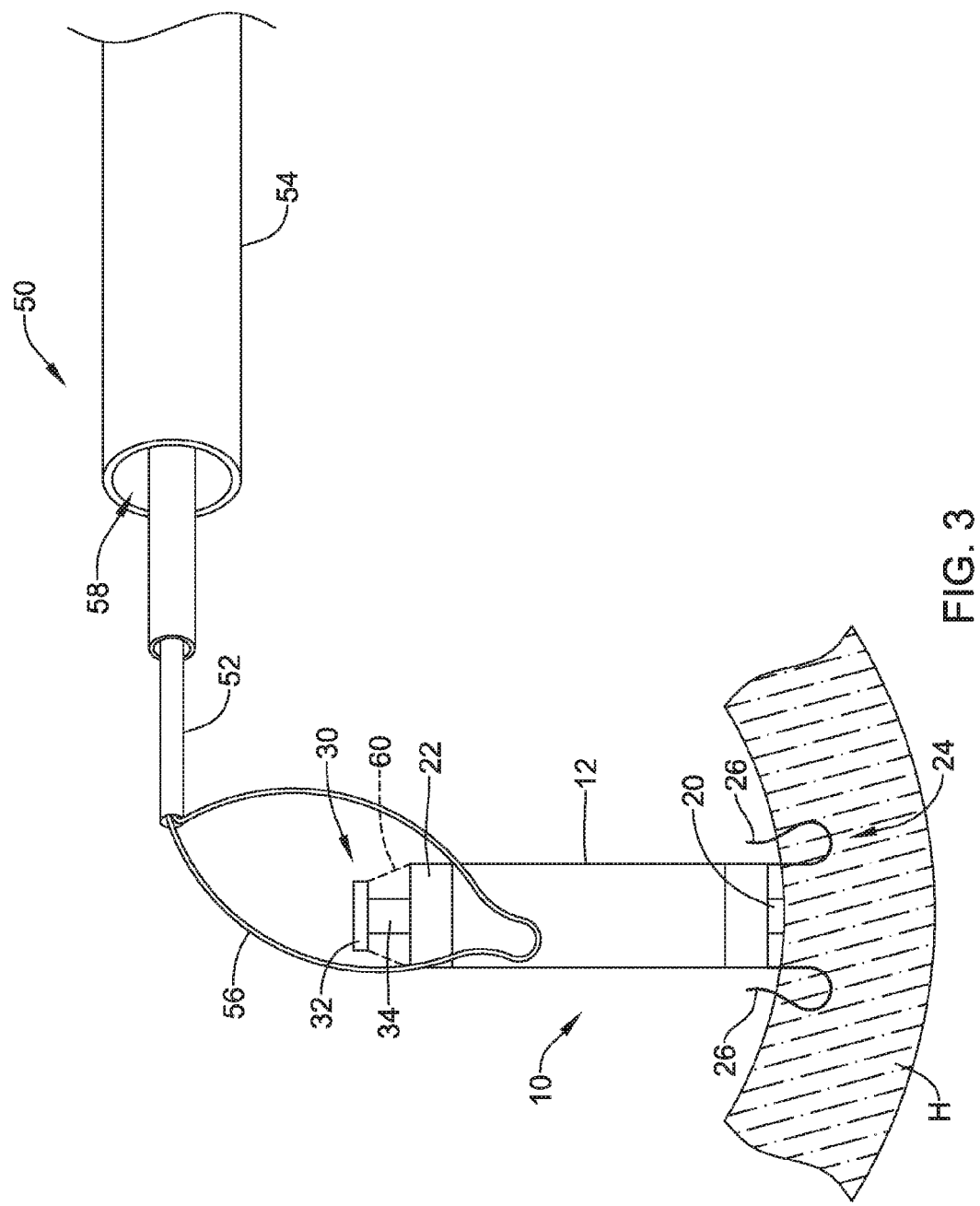
FIG. 3 illustrates another exemplary retrieval device capturing an implantable device during a retrieval procedure.

Another exemplary retrieval device 50 is illustrated in FIG. 3. Similar to FIG. 2, the retrieval device 50 may include a snare 52 advanceable from a lumen 58 of a retrieval catheter 54. The snare 52 may include one or more, or a plurality of loops 56 extending from a distal end of the snare 52 configured to engage the docking member 30 of the implantable device 10. The snare 52 shown in FIG. 3 includes a single loop 56 formed by an elongate filament extending from the shaft of the snare 52. Once the loop 56 of the snare 52 has captured the docking member 30, the snare 52 may be actuated proximally relative to the retrieval catheter 54 to pull the implantable device 10 into the lumen 58 of the retrieval catheter 54. The enlarged size of the head portion 32 relative to the neck portion 34 may permit the loop 56 of the snare 52 to encircle the neck portion 34 below (i.e., distal of) the head portion 32 and retain the loop 56 around the docking member 30 as the snare 52 is pulled proximally.

The loop of the snare 56 may collapse the covering 60 radially inward toward the neck portion 34 as the loop of the snare is cinched around the neck portion 34. The resiliency of the covering 60 may permit the loop of the snare 56 or other retrieval device to cinch around the neck portion 34 distal of the head portion 32 to secure the snare 56 with the docking member 30 to apply a retrieval force to pull the implantable device 10 into the retrieval catheter 54.

As the implantable device 10 is pulled into the retrieval catheter 54, the fixation mechanism 30 may disengage from the heart tissue to detach the implantable device 10 from the heart wall. For example, the hooks 26 may elongate as the implantable device 10 is drawn proximally into the lumen 58 of the retrieval catheter 54. Thereafter, the retrieval device 50, with the implantable device 10 captured in the lumen of the retrieval catheter 54 with the snare 52, may be withdrawn from the heart H.

Figure 4:
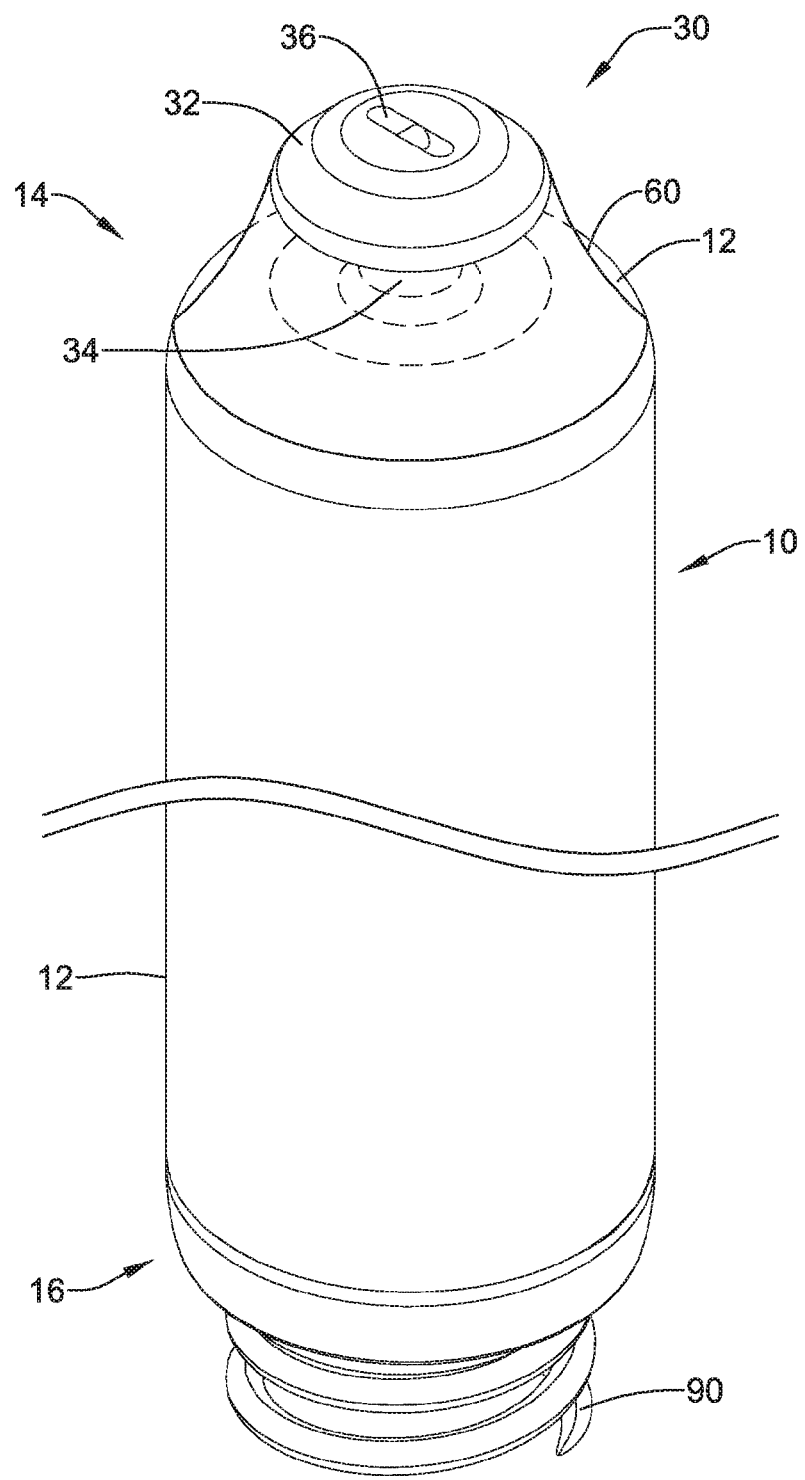
FIG. 4 illustrates an exemplary docking member of an implantable device including a covering surrounding at least a portion of the docking member.

FIG. 4 illustrates one exemplary docking member 30 with an associated covering 60 located at the proximal end 14 of the implantable device 10. The docking member 30 shown in FIG. 4 may include a head portion 32 and a neck portion 34 extending between the housing 12 and the head portion 32. The head portion 32 may be a generally disc shaped ball, having a radial dimension (e.g., diameter) greater than the radial dimension (e.g., diameter) of the neck portion 34. The docking member 30 may also include a passage 36 extending through a portion of the docking member 30 to receive a tether (not shown) which may be used in delivery and/or retrieval of the implantable device 10. For example, the passage 36 may extend through the head portion 32 from a first side to a second side of the head portion 32.

The covering 60 may be provided with the docking member 30. For example, the covering 60 may surround at least a portion of the neck portion 34 of the docking member 30 between the head portion 32 and the housing 12. The covering 60 may be configured to inhibit tissue growth or entanglement around the docking member 30 and/or preclude blood coagulation or embolization around the neck portion 34 while implanted in a patient, yet resilient to permit a snare or other retrieval device to cinch around the neck portion 34 during a retrieval procedure. For example, the covering 60 may deflect, compress, or otherwise collapse toward the longitudinal axis of the implantable device 10 by an applied force from the snare 56.

Figure 5A:
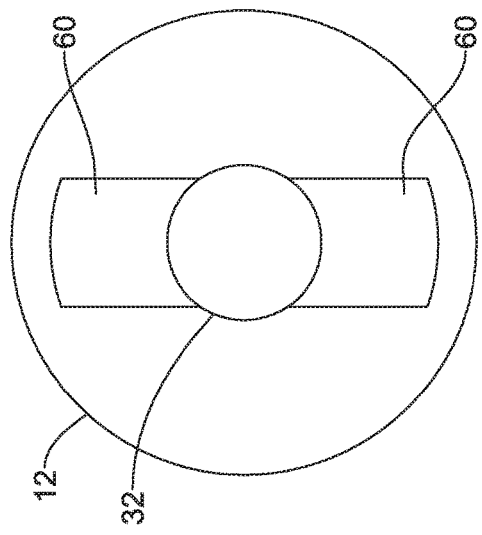
FIGS. 5A-5C are top views illustrating some exemplary configurations of a covering surrounding at least a portion of a docking member of an implantable device.
Figure 5B:
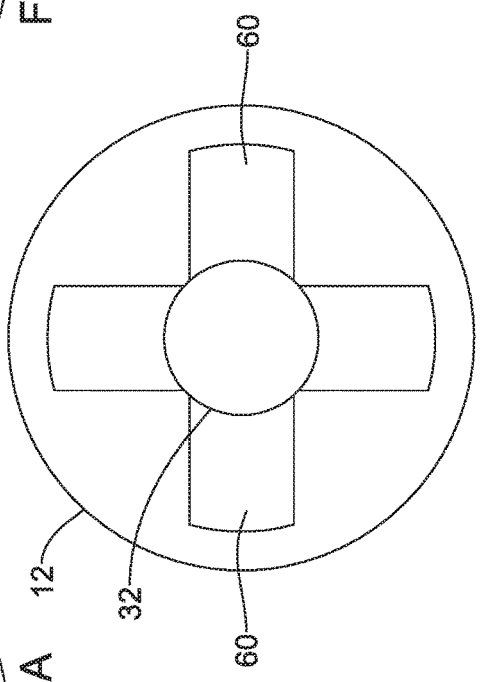
Figure 5C:
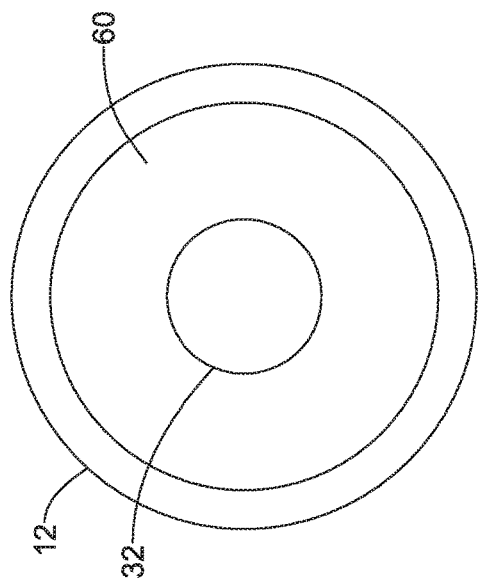

FIGS. 5A-5C are top views illustrating some exemplary configurations of the covering 60 surrounding at least a portion of the docking member 30 of the implantable device 10. These configurations are illustrative of some possible configurations, however, other configurations of the covering 60 are contemplated. As shown in FIG. 5A, in some embodiments, the covering 60 may be an annular member fully surrounding the entire perimeter of the neck portion 34 of the docking member 30. In other embodiments, such as in FIGS. 5B and 5C, the covering 60 may extend around less than the entire perimeter of the neck portion 34 of the docking member 30. For example, FIG. 5B illustrates a configuration of the covering 60 having a pair of regions extending in opposite directions from the docking member 30. FIG. 5C illustrates another configuration in which the covering 60 includes four regions equally arranged around the perimeter (e.g., circumference) of the neck portion 34 of the docking member 30. In embodiments in which the covering 60 includes one or more, or a plurality of segments, the segments may be arranged symmetrically or asymmetrically around the perimeter (e.g., circumference) of the neck portion 34, as desired.

The covering 60, which in some instances may be a shroud, collar, sheath, casing, or other structure covering or extending over at least portion of the neck portion 34 of the docking member 30, may be formed of any desired biocompatible material. For example, in some instances the covering 60 may include a fibrous material, such as an electrospun fibrous material, formed of one or more, or a plurality of nano-fibers. In some instances, the fibrous material may be a fabric or mesh material, formed of a plurality of non-woven, interwoven, entangled, or otherwise arranged fibers or filaments. In some instances, the covering 60 may include porous material having desired porosity. For example, the covering 60 may include a sponge material, such as synthetic sponge material, having an open cell or a closed cell structure which may be compressed with the application of force. In some instances, the covering 60 may include a foam material, such as an open-cell or closed-cell foam material having a desired porosity. For example, in some instances the foam material may be a reticulated foam material. In some instances, the covering 60 may include a gel.

The covering 60, which may be formed of one or more of the above configurations, or other desired configurations, may be formed of a biostable material and/or a bioabsorbable material. Some suitable biostable polymeric materials include, but are not necessarily limited to, polyamide, polyether block amide, polyethylene, polyethylene terephthalate, polypropylene, polyvinylchloride, polyurethane, polytetrafluoroethylene, polysulfone, and copolymers, blends, mixtures or combinations thereof. Examples of suitable bioabsorbable materials may include polymers, such as polylactide, poly-L-lactide (PLLA), polyglycolide (PGA), polylactide (PLA), poly-D-lactide (PDLA), polycaprolactone, polydioxanone, polygluconate, polylactic acid-polyethylene oxide copolymers, modified cellulose, collagen, poly(hydroxybutyrate), polyanhydride, polyphosphoester, poly(amino acids), and combinations thereof.

In some instances the covering 60 may include a therapeutic agent, if desired. The therapeutic agent may be a drug, a non-genetic agent, a genetic agent, etc. Some examples of suitable non-genetic therapeutic agents include but are not limited to: anti-thrombogenic agents such as heparin, heparin derivatives, urokinase, and PPack (dextrophenylalanine proline arginine chloromethylketone); anti-proliferative agents such as enoxaprin, angiopeptin, monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine and ropivacaine; anti-coagulants such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides; vascular cell growth promoters such as growth factor inhibitors, growth factor receptor antagonists, transcriptional activators, and translational promoters, vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin; bifunctional molecules consisting of an antibody and a cytotoxin; cholesterol-lowering agents; vasodilating agents; and agents which interfere with endogenous vasoactive mechanisms, and any combinations thereof.

FIGS. 6A-6B illustrate a first exemplary covering 60 for the docking member 30 of the implantable device 10. The covering 60 may extend from the docking member 30, for example the head portion 32 of the docking member 30, to the proximal end of the housing 12 of the implantable device 10, or otherwise be positioned between the head portion 32 and the housing 12. The covering 60 may extend across a recessed area 70 or hollow defined between the enlarged head portion 32 of the docking member 30 and a proximal end of the housing 12 of the implantable device 10. For example, the covering 60 may be a thin polymeric film extending across the recessed area 70. In the embodiment of FIGS. 6A-6B, a cavity 62 may be located between the covering 60 and an outer surface of the neck portion 34 of the docking member 30. In some instances, the covering 60 may extend entirely around the perimeter (e.g., circumference) of the docking member 30, or the covering 60 may be located around a portion of the perimeter of the docking member 30.

In the equilibrium state, shown in FIG. 6A, the covering 60 may have a radial dimension from the longitudinal axis X greater than the radial dimension of the neck portion 34. For example, the covering 60 may have a radial dimension from the longitudinal axis X greater than or equal to the radial dimension of the head portion 32. In embodiments in which the covering 60 annularly surrounds the neck portion 34, the collapsible covering 60 may have a first diameter in the equilibrium state.

The covering 60 may be collapsible toward the longitudinal axis, and thus toward the neck portion 34, to a collapsed state through the application of force, such as the cinching force of a snare 56 of a retrieval device, shown in FIG. 6B. In the collapsed state, shown in FIG. 6B, the radial dimension of the covering 60 in a plane perpendicular to the longitudinal axis X may be reduced from the radial dimension at the equilibrium state to a smaller radial dimension at the collapsed state. For example, in the collapsed state, shown in FIG. 6B, the diameter of the covering 60 in a plane perpendicular to the longitudinal axis X may be reduced from the first diameter at the equilibrium state to a second diameter smaller than the first diameter at the collapsed state.

Thus, the covering 60 may permit a loop of a snare 56 or other retrieval device, to engage the docking member 30 distal of the head portion 32 during a retrieval procedure and sufficiently tighten around the neck portion 34 such that the loop of the snare 56 will enter the recessed area 70 or hollow, and thus not slip off the docking member 30. For instance, the snare 56 may be sufficiently tightened around the neck portion 34 such that the head portion 32 is prevented from passing through the loop of the snare 56. For example, the snare 56 may be tightened in the recessed area 70 to a radial dimension less than the radial dimension of the head portion 32 in at least one radial direction from the longitudinal axis X, preventing the head portion 32 from passing through the loop of the snare 56. The collapsible covering 60 may inhibit tissue growth or entanglement around the docking member 30, such as in the recessed area 70, and/or preclude blood coagulation or embolization around the neck portion 34, such as in the recessed area 70, while implanted in a patient which may otherwise obstruct the recessed area 70 and thus inhibit the loop of the snare 56 from being sufficiently tightened around the docking member 30.

Figure 7B:
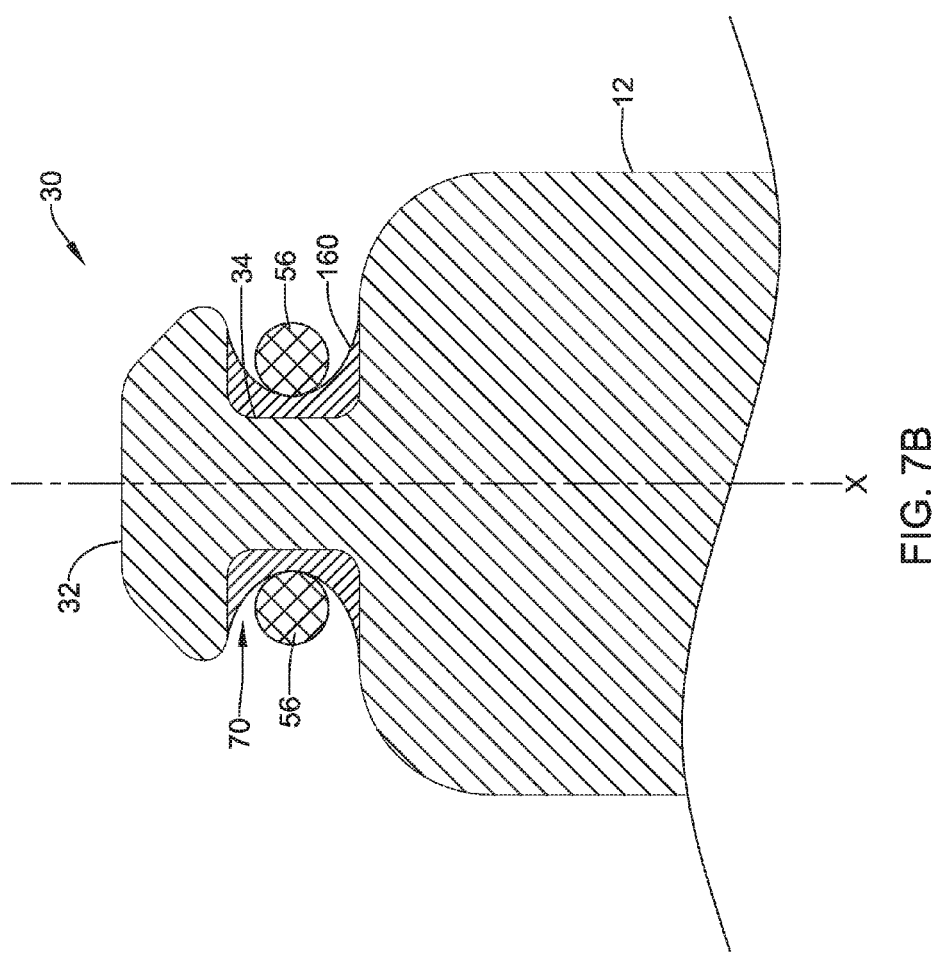

FIGS. 7A-7B illustrate a second exemplary covering 160 for the docking member 30 of the implantable device 10. The covering 160 may extend from the docking member 30, for example the head portion 32 of the docking member 30, to the proximal end of the housing 12 of the implantable device 10, or otherwise be positioned between the head portion 32 and the housing 12. The covering 160 may substantially fill a recessed area 70 or hollow defined between the enlarged head portion 32 of the docking member 30 and a proximal end of the housing 12 of the implantable device 10. In some instances, the covering 160 may be an annular member extending entirely around the perimeter (e.g., circumference) of the docking member 30 in the recessed area 70, or the covering 160 may be located around a portion of the perimeter of the docking member 30.

In the equilibrium state, shown in FIG. 7A, the covering 160 may have a radial dimension from the longitudinal axis X greater than the radial dimension of the neck portion 34. For example, the covering 160 may have a radial dimension from the longitudinal axis X greater than or equal to the radial dimension of the head portion 32. In embodiments in which the covering 160 annularly surrounds the neck portion 34, the collapsible covering 160 may have a first diameter in the equilibrium state.

The covering 160 may be collapsible toward the longitudinal axis, and thus toward the neck portion 34, to a collapsed state through the application of force, such as the cinching force of a snare 56 of a retrieval device, shown in FIG. 7B. In the collapsed state, shown in FIG. 7B, the radial dimension of the covering 160 in a plane perpendicular to the longitudinal axis X may be reduced from the radial dimension at the equilibrium state to a smaller radial dimension at the collapsed state. For example, in the collapsed state, shown in FIG. 7B, the diameter of the covering 160 in a plane perpendicular to the longitudinal axis X may be reduced from the first diameter at the equilibrium state to a second diameter smaller than the first diameter at the collapsed state.

Thus, the covering 160 may permit a loop of a snare 56 or other retrieval device, to engage the docking member 30 distal of the head portion 32 during a retrieval procedure and sufficiently tighten around the neck portion 34 such that the loop of the snare 56 will enter the recessed area 70 or hollow, and thus not slip off the docking member 30. For instance, the snare 56 may be sufficiently tightened around the neck portion 34 such that the head portion 32 is prevented from passing through the loop of the snare 56. For example, the snare 56 may be tightened in the recessed area 70 to a radial dimension less than the radial dimension of the head portion 32 in at least one radial direction from the longitudinal axis X, preventing the head portion 32 from passing through the loop of the snare 56. The collapsible covering 160 may inhibit tissue growth or entanglement around the docking member 30, such as in the recessed area 70, and/or preclude blood coagulation or embolization around the neck portion 34, such as in the recessed area 70, while implanted in a patient which may otherwise obstruct the recessed area 70 and thus inhibit the loop of the snare 56 from being sufficiently tightened around the docking member 30.

Figure 8B:
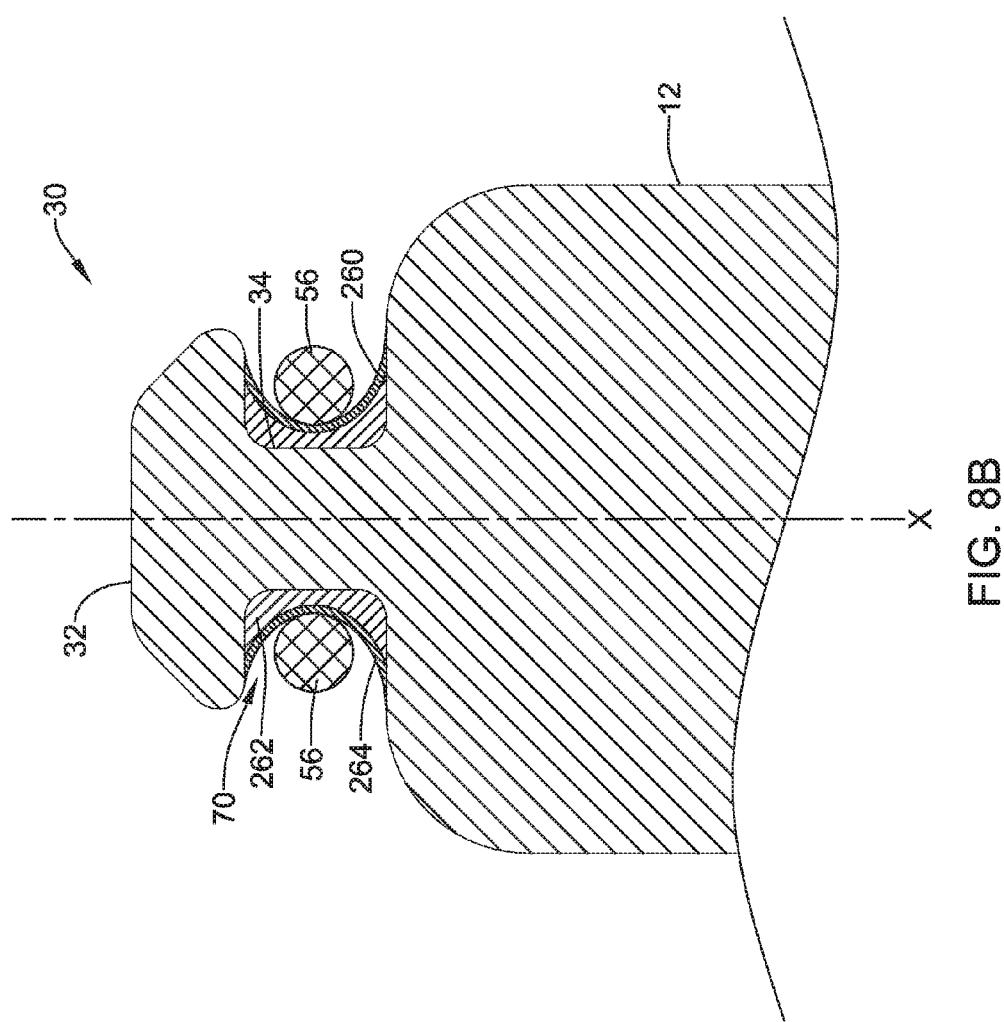

FIGS. 8A-8B illustrate a third exemplary covering 260 for the docking member 30 of the implantable device 10. The covering 260 may extend from the docking member 30, for example the head portion 32 of the docking member 30, to the proximal end of the housing 12 of the implantable device 10, or otherwise be positioned between the head portion 32 and the housing 12. The covering 260 may include an outer layer of material 264 and a core layer of material 262 radially interior of the outer layer 264. The covering 260 may substantially fill a recessed area 70 or hollow defined between the enlarged head portion 32 of the docking member 30 and a proximal end of the housing 12 of the implantable device 10. In some instances, the covering 260 may be an annular member extending entirely around the perimeter (e.g., circumference) of the docking member 30 in the recessed area 70, or the covering 260 may be located around a portion of the perimeter of the docking member 30. For example, the outer layer 264 may be an annular sleeve, with the inner layer 262 filling the space between the outer layer 264 and the neck portion 34 in the recessed area 70.

In the equilibrium state, shown in FIG. 8A, the covering 260 may have a radial dimension from the longitudinal axis X greater than the radial dimension of the neck portion 34. For example, the covering 260 may have a radial dimension from the longitudinal axis X greater than or equal to the radial dimension of the head portion 32. In embodiments in which the covering 260 annularly surrounds the neck portion 34, the collapsible covering 260 may have a first diameter in the equilibrium state.

The covering 260 may be collapsible toward the longitudinal axis, and thus toward the neck portion 34, to a collapsed state through the application of force, such as the cinching force of a snare 56 of a retrieval device, shown in FIG. 8B. In the collapsed state, shown in FIG. 8B, the radial dimension of the covering 260 in a plane perpendicular to the longitudinal axis X may be reduced from the radial dimension at the equilibrium state to a smaller radial dimension at the collapsed state. For example, in the collapsed state, shown in FIG. 8B, the diameter of the covering 260 in a plane perpendicular to the longitudinal axis X may be reduced from the first diameter at the equilibrium state to a second diameter smaller than the first diameter at the collapsed state.

Thus, the covering 260 may permit a loop of a snare 56 or other retrieval device, to engage the docking member 30 distal of the head portion 32 during a retrieval procedure and sufficiently tighten around the neck portion 34 such that the loop of the snare 56 will enter the recessed area 70 or hollow, and thus not slip off the docking member 30. For instance, the snare 56 may be sufficiently tightened around the neck portion 34 such that the head portion 32 is prevented from passing through the loop of the snare 56. For example, the snare 56 may be tightened in the recessed area 70 to a radial dimension less than the radial dimension of the head portion 32 in at least one radial direction from the longitudinal axis X, preventing the head portion 32 from passing through the loop of the snare 56. The collapsible covering 260 may inhibit tissue growth or entanglement around the docking member 30, such as in the recessed area 70, and/or preclude blood coagulation or embolization around the neck portion 34, such as in the recessed area 70, while implanted in a patient which may otherwise obstruct the recessed area 70 and thus inhibit the loop of the snare 56 from being sufficiently tightened around the docking member 30.

FIGS. 9A-9E illustrate another exemplary covering 360 for a docking member 30 of an implantable device 10. The covering 360 may extend from the docking member 30, for example the head portion 32 of the docking member 30, to the proximal end of the housing 12 of the implantable device 10, or otherwise be positioned between the head portion 32 and the housing 12. The covering 360 may substantially fill a recessed area 70 or hollow defined between the enlarged head portion 32 of the docking member 30 and a proximal end of the housing 12 of the implantable device 10. In some instances, the covering 360 may be an annular member extending entirely around the perimeter (e.g., circumference) of the docking member 30 in the recessed area 70, or the covering 360 may be located around a portion of the perimeter of the docking member 30.

In the equilibrium state, shown in FIG. 9A, the covering 360 may have a radial dimension from the longitudinal axis X greater than the radial dimension of the neck portion 34. For example, the covering 360 may have a radial dimension from the longitudinal axis X greater than or equal to the radial dimension of the head portion 32. In embodiments in which the covering 360 annularly surrounds the neck portion 34, the collapsible covering 360 may have a first diameter in the equilibrium state.

Figure 9E:
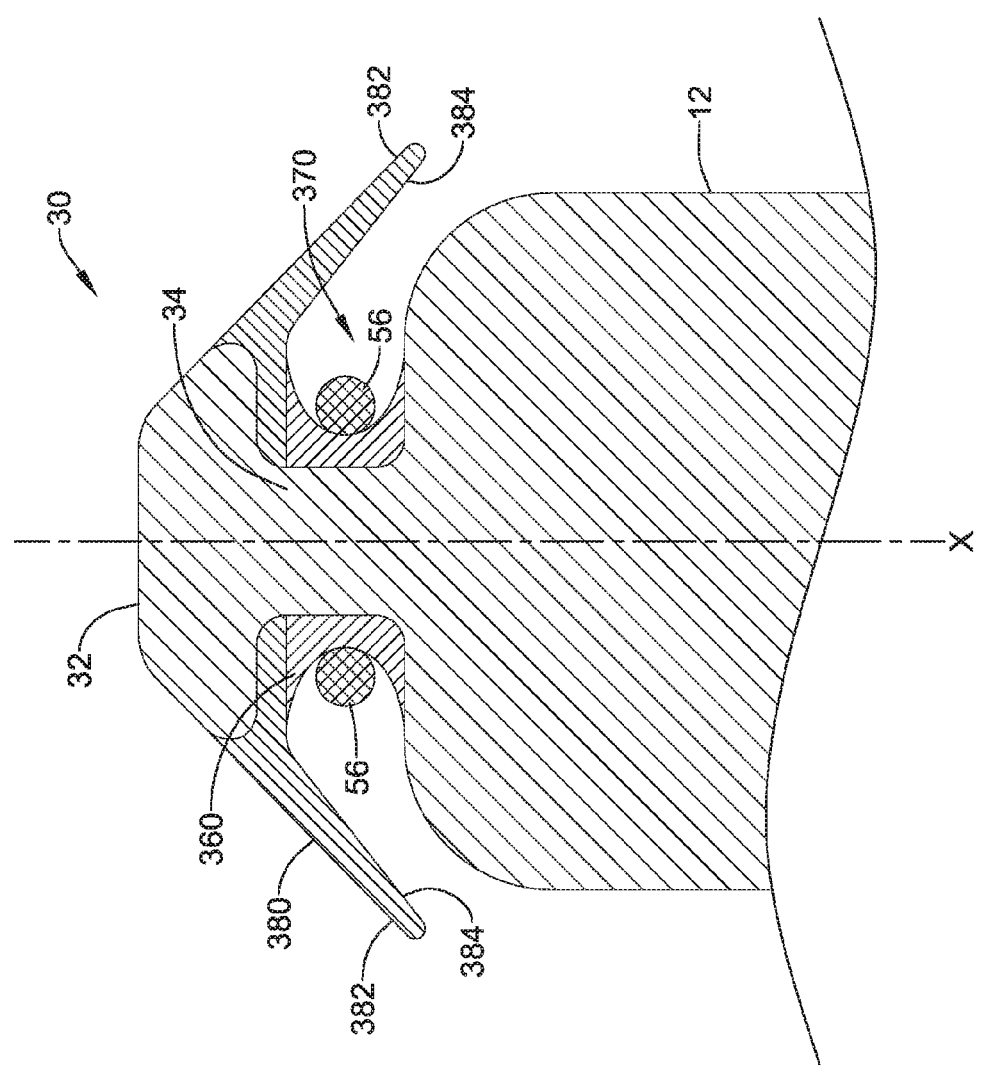

The covering 360 may be collapsible toward the longitudinal axis, and thus toward the neck portion 34, to a collapsed state through the application of force, such as the cinching force of a snare 56 of a retrieval device, shown in FIG. 9E. In the collapsed state, shown in FIG. 9E, the radial dimension of the covering 360 in a plane perpendicular to the longitudinal axis X may be reduced from the radial dimension at the equilibrium state to a smaller radial dimension at the collapsed state. For example, in the collapsed state, shown in FIG. 9E, the diameter of the covering 360 in a plane perpendicular to the longitudinal axis X may be reduced from the first diameter at the equilibrium state to a second diameter smaller than the first diameter at the collapsed state.

Thus, the covering 360 may permit a loop of a snare 56 or other retrieval device, to engage the docking member 30 distal of the head portion 32 during a retrieval procedure and sufficiently tighten around the neck portion 34 such that the loop of the snare 56 will enter the recessed area 70 or hollow, and thus not slip off the docking member 30. For instance, the snare 56 may be sufficiently tightened around the neck portion 34 such that the head portion 32 is prevented from passing through the loop of the snare 56. For example, the snare 56 may be tightened in the recessed area 70 to a radial dimension less than the radial dimension of the head portion 32 in at least one radial direction from the longitudinal axis X, preventing the head portion 32 from passing through the loop of the snare 56. The collapsible covering 360 may inhibit tissue growth or entanglement around the docking member 30, such as in the recessed area 70, and/or preclude blood coagulation or embolization around the neck portion 34, such as in the recessed area 70, while implanted in a patient which may otherwise obstruct the recessed area 70 and thus inhibit the loop of the snare 56 from being sufficiently tightened around the docking member 30.

The covering 360 may also include one or more retrieval features configured to direct a retrieval device into the recessed area 70 and into engagement with the docking member 30. For example, the covering 360 may include a retrieval member 380 including one or more, or a plurality of radially extending protrusions 382. As shown in FIG. 9A, the radially extending protrusion(s) may extend a radial distance D2 greater than the radial distance D1 of the housing 12 in an equilibrium or deployed state. The protrusion(s) 382 may include an engagement surface 384, such as an angled engagement surface 384. The engagement surface 384 may be oriented at an oblique angle to the longitudinal axis X to facilitate guiding a snare 56 of a retrieval device into the recessed area 70.

In a delivery state, such as shown in FIG. 9B, the protrusion(s) may deflect within a delivery sheath 90, and expand outward to the equilibrium position shown in FIG. 9A when deployed.

During retrieval of the implantable device 10 with a snare 56 of a retrieval device, the snare 56 may be manipulated to surround the housing 12 of the implantable device 10, shown in FIG. 9C. Once the snare 56 has encircled the housing 12, the snare 56 may be cinched down around the housing 12 and drawn proximally toward the docking member 30, as shown in FIG. 9C. Turning the FIG. 9D, as the snare 56 reaches the protrusion(s) 382, the snare 56 may engage the engagement surface 384 of the protrusion(s) 382 to guide the snare 56 into the recessed area 70. The retrieval member 380 may prevent the snare 56 from slipping off of the docking member 30.

With the snare 56 guided into the recessed area 70, the loop of the snare 56 may be cinched down around the neck portion 34, thus collapsing the covering 360 radially inward toward the neck portion 34.

Those skilled in the art will recognize that aspects of the present disclosure may be manifested in a variety of forms other than the specific embodiments described and contemplated herein. Accordingly, departure in form and detail may be made without departing from the scope and spirit of the present disclosure as described in the appended claims.

ADDITIONAL EXAMPLES

One additional example is an implantable leadless cardiac pacing device including a housing having a proximal end and a distal end, an electrode positioned proximate the distal end of the housing configured to be positioned adjacent cardiac tissue, and a docking member extending from the proximal end of the housing along a longitudinal axis of the housing. The docking member is configured to facilitate retrieval of the implantable leadless cardiac pacing device. The docking member includes a head portion and a neck portion extending between the housing and the head portion. The head portion has a radial dimension from the longitudinal axis and the neck portion has a radial dimension from the longitudinal axis less than the radial dimension of the head portion. A covering surrounds at least a portion of the neck portion of the docking member.

Additionally or alternatively, in a second embodiment, the covering precludes blood coagulation or embolization around the neck portion while implanted in a patient.

Additionally or alternatively, in a third embodiment, the covering is collapsible toward the neck portion.

Additionally or alternatively, in a fourth embodiment, the covering extends from the head portion of the docking member to the proximal end of the housing.

Additionally or alternatively, in a fifth embodiment, the covering has a radial dimension from the longitudinal axis greater than the radial dimension of the neck portion.

Additionally or alternatively, in a sixth embodiment, the covering has a radial dimension from the longitudinal axis greater than or equal to the radial dimension of the head portion.

Additionally or alternatively, in a seventh embodiment, the covering comprises an electro-spun fibrous material.

Additionally or alternatively, in an eighth embodiment, the covering comprises a synthetic sponge material.

Additionally or alternatively, in a ninth embodiment, the covering comprises a foam material.

Additionally or alternatively, in a tenth embodiment, the covering comprises a gel.

Additionally or alternatively, in an eleventh embodiment, the covering comprises a fabric material.

Additionally or alternatively, in a twelfth embodiment, the covering comprises a bioabsorbable material.

Additionally or alternatively, in a thirteenth embodiment, the covering comprises a drug.

Additionally or alternatively, in a fourteenth embodiment, the covering includes one or more retrieval features configured to direct a retrieval device into engagement with the docking member.

Additionally or alternatively, in a fifteenth embodiment, the one or more retrieval features include one or more radially extending protrusions.

What is claimed is:

1. An implantable leadless cardiac pacing device comprising:
   a housing having a proximal end, a distal end, and a circumferential surface extending between the proximal end and the distal end;
   an electrode positioned proximate the distal end of the housing configured to be positioned adjacent cardiac tissue;
   a docking member extending from the proximal end of the housing along a longitudinal axis of the housing, the docking member configured to facilitate retrieval of the implantable leadless cardiac pacing device; and
   a covering affixed to the docking member, the covering surrounding at least a portion of the docking member and including one or more retrieval features having a radial dimension from the longitudinal axis greater than a radial dimension of the housing from the longitudinal axis to the circumferential surface of the housing;
   wherein the covering is configured to remain affixed to the docking member while implanted in a patient.

2. The implantable leadless cardiac pacing device of claim 1, wherein the one or more retrieval features are configured to direct a retrieval device into engagement with the docking member.

3. The implantable leadless cardiac pacing device of claim 2, wherein the one or more retrieval features are further configured to prevent a head portion of the docking member from passing through the retrieval device.

4. The implantable leadless cardiac pacing device of claim 1, wherein the one or more retrieval features include one or more radially extending protrusions.

5. The implantable leadless cardiac pacing device of claim 4, wherein the one or more radially extending protrusions each include an engagement surface configured to facilitate guiding a retrieval device into engagement with the docking member.

6. The implantable leadless cardiac pacing device of claim 5, wherein the engagement surface is oriented at an oblique angle to the longitudinal axis.

7. The implantable leadless cardiac pacing device of claim 4, wherein the one or more radially extending protrusions are configured to deflect to a delivery state and expand to an equilibrium state.

8. The implantable leadless cardiac pacing device of claim 7, wherein the radial dimension of the one or more retrieval features is greater than the radial dimension of the housing when the one or more radially extending protrusions are in the equilibrium state.

9. The implantable leadless cardiac pacing device of claim 1, wherein the docking member includes a head portion and a neck portion extending between the housing and the head portion, the head portion having a radial dimension from the longitudinal axis and the neck portion having a radial dimension from the longitudinal axis less than the radial dimension of the head portion.

10. The implantable leadless cardiac pacing device of claim 9, wherein the covering surrounds the head portion of the docking member.

11. The implantable leadless cardiac pacing device of claim 9, wherein the radial dimension of the one or more retrieval features is greater than the radial dimension of the head portion.

12. The implantable leadless cardiac pacing device of claim 9, wherein the covering surrounds the neck portion of the docking member.

13. The implantable leadless cardiac pacing device of claim 1, wherein the one or more retrieval features are angled toward the distal end of the housing.

14. An implantable leadless cardiac pacing device comprising:
a housing having a proximal end, a distal end, and a circumferential surface extending between the proximal end and the distal end;
an electrode positioned proximate the distal end of the housing configured to be positioned adjacent cardiac tissue;
a docking member extending from the proximal end of the housing along a longitudinal axis of the housing, the docking member configured to facilitate retrieval of the implantable leadless cardiac pacing device;
the docking member including a head portion and a neck portion extending between the housing and the head portion;
the head portion having a radial dimension from the longitudinal axis and the neck portion having a radial dimension from the longitudinal axis less than the radial dimension of the head portion; and
one or more flexible retrieval features extending from the head portion of the docking member configured to direct a retrieval device into engagement with the docking member, the one or more flexible retrieval features configured to deflect from an equilibrium state to a delivery state.

15. The implantable leadless cardiac pacing device of claim 14, wherein the one or more flexible retrieval features include one or more radially extending protrusions.

16. The implantable leadless cardiac pacing device of claim 15, wherein the one or more radially extending protrusions have a radial dimension from the longitudinal axis in the equilibrium state greater than a radial dimension of the housing from the longitudinal axis to the circumferential surface of the housing.

17. The implantable leadless cardiac pacing device of claim 14, wherein the one or more flexible retrieval features include a plurality of radially extending protrusions extending radially from the head portion of the docking member.

18. The implantable leadless cardiac pacing device of claim 17, wherein the plurality of radially extending protrusions are oriented at an oblique angle to the longitudinal axis.

19. The implantable leadless cardiac pacing device of claim 18, wherein the plurality of radially extending protrusions are angled toward the distal end of the housing.

20. A method of retrieving an implantable cardiac pacing device, the implantable cardiac pacing device having a housing having a proximal end, a distal end, and a circumferential surface extending between the proximal end and the distal end, an electrode positioned proximate the distal end of the housing, and a docking member extending from the proximal end of the housing along a longitudinal axis of the housing, the docking member including a head portion, a neck portion extending between the housing and the head portion, and one or more flexible retrieval features extending from the head portion of the docking member, the one or more flexible retrieval features configured to deflect from an equilibrium state to a delivery state, the method comprising:
advancing a snare toward the docking member such that the snare engages an engagement surface of the one or more flexible retrieval features and the engagement surface
guiding the snare along the engagement surface into a recess area between the engagement surface and the neck portion of the docking member; and
cinching the loop around the neck portion of the docking member.

* * * * *